US006447478B1

(12) United States Patent
Maynard

(10) Patent No.: US 6,447,478 B1
(45) Date of Patent: Sep. 10, 2002

(54) THIN-FILM SHAPE MEMORY ALLOY ACTUATORS AND PROCESSING METHODS

(76) Inventor: Ronald S. Maynard, 316 Gardenia Dr., San Jose, CA (US) 95123

( * ) Notice: Subject to any disclaimer, the term of this patent is extended or adjusted under 35 U.S.C. 154(b) by 0 days.

(21) Appl. No.: 09/079,703

(22) Filed: May 15, 1998

(51) Int. Cl.[7] ............................................ A61M 37/00

(52) U.S. Cl. ..................... 604/95.05; 604/531; 600/151

(58) Field of Search ........................... 604/95.04, 95.05, 604/523, 528, 530, 531, 113, 114, 264, 533–535; 600/139, 143, 146, 151, 141; 623/1.18, 1.19

(56) References Cited

U.S. PATENT DOCUMENTS

| | | | | |
|---|---|---|---|---|
| 2,790,606 A | | 4/1957 | Morgan et al. | |
| 4,753,223 A | * | 6/1988 | Bremer | 600/140 |
| 5,325,845 A | * | 7/1994 | Adair | 600/114 |
| 5,405,337 A | * | 4/1995 | Maynard | 604/281 |
| 5,624,380 A | * | 4/1997 | Takayama et al. | 600/146 |
| 2001/0039413 A1 | * | 11/2001 | Bowe | 604/532 |

FOREIGN PATENT DOCUMENTS

| | | | | |
|---|---|---|---|---|
| DE | 1 601 197 | | 5/1970 | |
| DE | 17 76 252 | | 7/1977 | |
| DE | 33 25 230 | | 3/1994 | |
| GB | 2 175 685 | | 12/1986 | |
| WO | WO 99/60267 | * | 11/1999 | F03G/7/06 |

* cited by examiner

*Primary Examiner*—Brian L. Casler
*Assistant Examiner*—Catherine Serke
(74) *Attorney, Agent, or Firm*—Skjerven Morrill LLP

(57) ABSTRACT

A shape memory alloy actuator array comprising a plurality of individually trained shape memory alloy actuators to provide relative movement of different actuator array portions and a thin-film heating element positioned adjacent at least one shape memory alloy actuator to thermally activate the actuator for movement away from its initial shape. A shape memory alloy medical device such as a catheter or a conduit is further provided comprising a lattice network or scaffolding of individually activated and oppositely trained shape memory alloy actuators set with a predetermined shape to provide a full range of directional movement within a body, and a network of thin-film heating elements to selectively activate a combination of actuators for movement or variable stiffness. A method of forming a shape memory alloy actuator array is also provided wherein a plurality of shape memory alloy actuators are formed by removing selected window portions from a single sheet of shape memory alloy along a series of spaced apart rows and columns before individual training with a predetermined shape. A thin-film network of addressable heating elements may further be deposited onto the sheet for selective activation of shape memory alloy actuators within the array.

24 Claims, 16 Drawing Sheets

300
310
320
330
10

THIN-FILM SHAPE MEMORY ALLOY ACTUATORS AND PROCESSING METHODS

FIELD OF THE INVENTION

The present invention is generally directed to apparatus and related methods for providing highly maneuverable shape memory alloy devices. More particularly, the present invention relates to devices with separately addressable thin-film shape memory alloy actuators.

BACKGROUND OF THE INVENTION

Shape memory alloys are a unique group of materials that exhibit memory retentive properties. A shape memory alloy element may be trained with a high temperature shape, and may also have a relatively deformable low temperature shape. Changes in surrounding temperatures result in a phase transformation in its crystalline structure. At lower temperatures, shape memory alloys are relatively deformable and exist in what is known as a martensitic phase. Meanwhile, at higher temperatures, these materials experience a phase transformation towards an austenitic phase which is more rigid and inflexible. The temperature at which the phase transition occurs is referred to as the activation temperature. A shape memory alloy element may be initially imprinted or trained with a particular configuration when heated to a temperature much higher than the transition temperature. Shape memory alloys have been observed to repeatedly recover their memory shape when heated above their respective transition temperatures very rapidly, and with great constant force over a wide range of retentive strain energy. The ability of shape memory alloys to remember their high temperature trained shape makes them particularly suitable for actuating devices that provide useful work and directional movement.

The basis for selecting shape memory alloys in the construction of conventional steerable elements such as a flexible catheters is primarily their ability to reversibly change shapes during their microstructural transformation. At lower temperatures, shape memory alloys are relatively soft and may exhibit a Young's modulus of approximately 3000 MPa. In a martensitic phase, the shape memory alloy may be readily deformed up to about 5% in any direction without adversely affecting its memory properties. When heated just beyond its activation temperature, the transformation process commences, and the material becomes a harder, inflexible material that may have a Young's modulus of approximately 6900 MPa in an austenite or parent phase. When the shape memory alloy material is not excessively deformed or constrained, it attempts to reorganize its structure to a previously trained or memorized shape. Upon cooling, the shape memory alloy again, becomes soft and may be mechanically deformed to begin another cycle. The mechanical deflections produced by activating the memorized state can produce useful work if suitably configured in apparatus such as actuation devices. Although the measurable recovery deflections may be relatively small, the recovery forces and energy have been observed to be extremely high and constant.

A common example of a shape memory alloy includes nickel titanium alloys (NiTi), also known as nitinol, which may vary in relative percentages of composition. The activation temperature of a particular shape memory alloy may be changed according to its elemental composition. When the alloy is heated through its transformation temperature, it reverts back to its austenite phase, and recovers its shape with great force. The temperature at which the material remembers its high temperature form may be adjusted by changes in alloy composition and specific heat treatment. For example, activation temperatures for NiTi alloys may be readily altered from 100° C. above or below zero. The shape recovery process, however, may be controlled and occur over a range of just a few degrees or less if necessary. A wide variety of shapes may be programmed into an shape memory alloy actuator element by physically constraining the piece while heating it to an appropriate annealing temperature. NiTi is commercially available in sheet, tube and wire forms, and may have a wide range of transformation temperatures. The memory transformation of an shape memory alloy element is dependent upon temperature. However, the rate of deformation is largely dependent upon the rate of cooling and heating. The rate at which temperature changes take place often dictates the relative speed at which the actuator can operate. A faster actuating shape memory alloy actuator must often be heated and cooled more readily, and has been known to consume more power and generate an excess amount of dissipated heat.

Shape memory alloy actuators have been used in numerous steerable devices such as catheters. These devices are limited in dexterity, however, and movement is often limited to a single plane and not in a rotational direction. Shape memory alloy elements must also be mechanically deformed to begin another cycle. Each shape memory element is often coupled to a biasing element or at least one other shape memory element. When one of the elements is heated and moves towards its predetermined shape, it is returned to an original position or shape by the biasing element or the activation of another memory element. This generally enables controlled motion but only in a single plane, and may provide only up to two degrees of freedom. Moreover, the relative dimensions of actuator joints are often excessively large and cumbersome since an opposite force is needed to return the shape memory alloy element to its initial martensitic shape. In general, complex linkages are also required to rotate these steerable devices. The range of maneuverability is severely limited by the linkages which are necessary to return the element to its martensitic shape after it has been activated and cooled. Conventional steerable devices using shape memory alloys are also relatively large and have a severely constrained lower size limit. The relatively large size of present actuators is mainly attributed to sizeable control arms, linkages or other elements needed to return the shape memory actuator to its initial state. This severely constrains the geometry of such a conventional steerable device. Available shape memory alloy devices today also lack the precise control necessary to maneuver into very small, geometrically complex spaces. Moreover, current actuators are often too slow for many medical applications where quick, dexterous movement is required. Large steerable devices with shape memory alloy elements often require an increased amount of current in order to produce the activation temperature needed for a quick transition from the martensitic state to the programmed or memorized austenitic phase. A conventional shape memory alloy actuator consumes a great deal of power, thus dissipating a large amount of heat. This necessarily slows down the cooling to the activation threshold, and slows down the transition from the austenitic state back to the martensitic state resulting in a slower acting device.

There is a need for an efficient actuator device that is capable of unrestricted yet highly precise and dexterous maneuvers in three-dimensional space. It would be advantageous to reduce the need for control arms, linkages, or other extraneous mechanical devices for returning conventional shape memory alloy elements to a first position after deactivation, and their transition from the parent phase back to the martensitic state. There is a further need for shape memory alloy actuators that provide unrestricted linear and rotational movement. These devices should be saleable to provide increased dexterity and maneuverability in very small, geometrically constrained areas which are presently inaccessible by conventional steerable devices. An effective heating system is further required to activate highly detailed actuator patterns formed from shape memory alloys or any other material with memory capability. It would further desirable to form a variety of actuator arrays from a minimum number of shape memory alloy sheets to simplify the production and the assembly process.

SUMMARY OF THE INVENTION

The present invention provides shape memory alloy actuator apparatus and related processing methods. An object of the invention is to provide shape memory alloy apparatus with a full range of linear and rotational movement with variable stiffness.

In one embodiment of the invention, a shape memory alloy actuator array is formed from a plurality of individually trained shape memory alloy actuators to provide relative movement of different array portions, and a thin-film heating element positioned adjacent at least one shape memory alloy actuator to thermally activate the actuator for movement away from its initial shape. The shape memory alloy actuators m,ay be positioned in between at least two connecting rings and adjacent another shape memory alloy actuator along a different portion of the connecting rings. The actuators may be further positioned in side by side pairs with a biasing element for returning the actuator to its initial shape. The side by side pairs may be formed along the periphery of the connection rings and include one actuator that expands or extends towards a predetermined shape when heated and one actuator that contracts towards a predetermined shape when heated. Alternatively, the plurality of shape memory alloy actuators may be positioned to act in opposition to at least one other actuator formed of shape memory alloy, elastomer material or a spring. The total number of shape memory alloy actuators that are trained to expand when activated may be equal to or different than the total number of shape memory alloy actuators that are trained to contract when activated.

An additional object of the present invention is to provide a shape memory alloy array with actuators having initial nonplanar shapes and substantially planar predetermined shapes. The shape memory alloy actuators may also have an initial buckled shape that provides useful work when activated towards its substantially planar predetermined shape. The buckled configuration of the shape memory actuators exploit certain advantages of force amplification to effect relative movement of different array portions.

It is a further object of the present invention to vary the stiffness of a shape memory alloy device through the activation of a combination of at least one actuator.

Another embodiment of the present invention provides a shape memory alloy catheter comprising a catheter body formed with a sidewall portion, a shape memory alloy portion positioned adjacent the catheter sidewall portion having a lattice network of individually configured shape memory alloy micro-actuators, and an addressable thin-film heater element in communication with the shape memory alloy portion for activation of selected micro-actuators. More particularly, the shape memory alloy catheter may further include connecting rings or intermediary spacers for separating the device into segmented joints with at least one micro-actuator that expands upon heating by an addressable heater element, and at least one micro-actuator that contracts upon heating by another addressable heater element. A selected combination of at least one micro-actuator may be activated for varying the relative stiffness of the shape memory alloy portion.

Another variation of the present invention is directed to a shape memory alloy conduit comprising a lattice structure formed of shape memory alloy micro-actuators, and a network of heating elements formed about the lattice structure for activating selected shape memory actuators within the lattice structure. The network of heating elements activates a selected combination of at least one actuator in the conduit which may provide relative movement between conduit portions, or vary the relative stiffness of lattice structure portions. The lattice structure may include connecting rings with intermediary shape memory alloy micro-actuators that may expand or contract when heated. The network of heating elements may be thin-film addressable heating elements controlled by a microprocessor unit that selectively activates a combination of at least one micro-actuator for relative movement of the shape memory alloy conduit or for variable stiffness.

In yet another embodiment of the present invention, a shape memory alloy apparatus and associated methods provide a shape memory alloy medical device comprising a scaffolding formed of individually activated and oppositely trained shape memory alloy actuators set with a predetermined shape to provide a full range of directional movement within a body, and at least one heating element in communication with the scaffolding surface to selectively activate a combination of at least one actuator towards a predetermined state. The scaffolding may include at least two connecting rings to support relative movement of the shape memory alloy medical device. The actuators within the scaffolding may have substantially rectangular configuration with a buckled surface longitudinally and laterally aligned relative to the scaffolding. It is a further object of the invention to provide a system of separately addressable thin-film heaters that thermally activates a selected combination of at least one actuator to vary the ring to ring tilt or rotational angle of the scaffolding within a predetermined range. The plurality of heating elements may also thermally activate a selected combination of at least one trained actuator towards an intermediate state for variable stiffness and relative movement of the device within the body.

It is another object of this invention to provide a directional actuator device comprising a skeletal structure formed of oppositely trained shape memory alloy actuators each configured with a predetermined shape, and a heating system having individual localized heaters for moving each actuator towards its predetermined shape. The skeletal structure may further include a backbone and a shape memory alloy portion that contracts when thermally activated, and a shape memory alloy portion that expands when thermally activated to provide for arcuate movement of the actuator device. The skeletal structure may be further formed with a supporting ribbed cage section. At least a portion of the directional actuator may be encapsulated within at least one polymeric coating.

Another embodiment of the present invention includes a thermally activated directional actuator device with a skeletal structure and a plurality of intermediary spacers or connecting rings for supporting relative movement of the directional actuator portions. The intermediary spacers may further include actuator extensions for connection to actuators. The skeletal structure may be formed with at least two oblong actuators longitudinally aligned relative to the structure and at least two oblong actuators laterally aligned relative to the structure for relative movement of the skeletal structure portion. The connecting rings may be formed with actuator extensions for connecting actuators laterally aligned relative to the actuator device. The laterally aligned actuators may also include at least one actuator that expands in length when heated and at least one actuator that contracts in length when heated.

It is a further object of the present invention to provide a method of forming a shape memory alloy actuator device comprising the following steps of: selecting a sheet of shape memory alloy material defined by at least two side edges; forming a plurality of shape memory alloy actuators to provide relative movement of the actuator by removing selected window portions of the sheet along a series of spaced apart rows and columns; individually training the shape memory alloy actuators to a predetermined state; laying out a thin-film network of addressable heating elements onto the sheet for selectively activating the shape memory alloy actuators; and sealing the side edges of the sheet to form a shape memory alloy actuator array. The spaced apart rows may form connecting rings to support relative movement of the shape memory alloy actuator array. The spaced apart columns may generally define the lateral portions of the shape memory alloy actuators. The plurality of shape memory alloy actuators may also be formed in side by side pairs. Each trained shape memory alloy actuator may move towards a predetermined shape by heating, and may be trained to expand or to contract when activated. The network of addressable heating elements may also be connected to a microprocessor unit for selectively activating a combination of at least one shape memory alloy actuator.

In yet another embodiment of the present invention, an additional thin-film sheet of shape memory alloy material may be selected to provide for an actuator formed of multiple sheets. The shape memory alloy actuators formed in the first thin-film sheet may be trained to expand when heated, and the shape memory alloy actuators formed in the second thin-film sheet may be trained to contract when heated. These and other objects and advantages of the present invention will become more apparent from the following description and accompanying drawings.

DETAILED DESCRIPTION OF THE INVENTION

The present invention provides shape memory alloy actuator apparatus and related processing methods. It should be understood that the following description of the invention includes various embodiments that are suitable for a wide variety of applications including medical device systems and their manufacture. Any type of shape memory alloy may be selected for the following apparatus and methods including nickel titanium alloys (NiTi), or what is commonly known as nitinol, copper nickel aluminum, or copper zinc aluminum. Other types of materials that demonstrate memory retentive properties may also be used to form the various actuator configurations and activation systems provided herein. Each of the disclosed embodiments may be considered individually or in combination with other variations and aspects of the invention.

Figure 1:
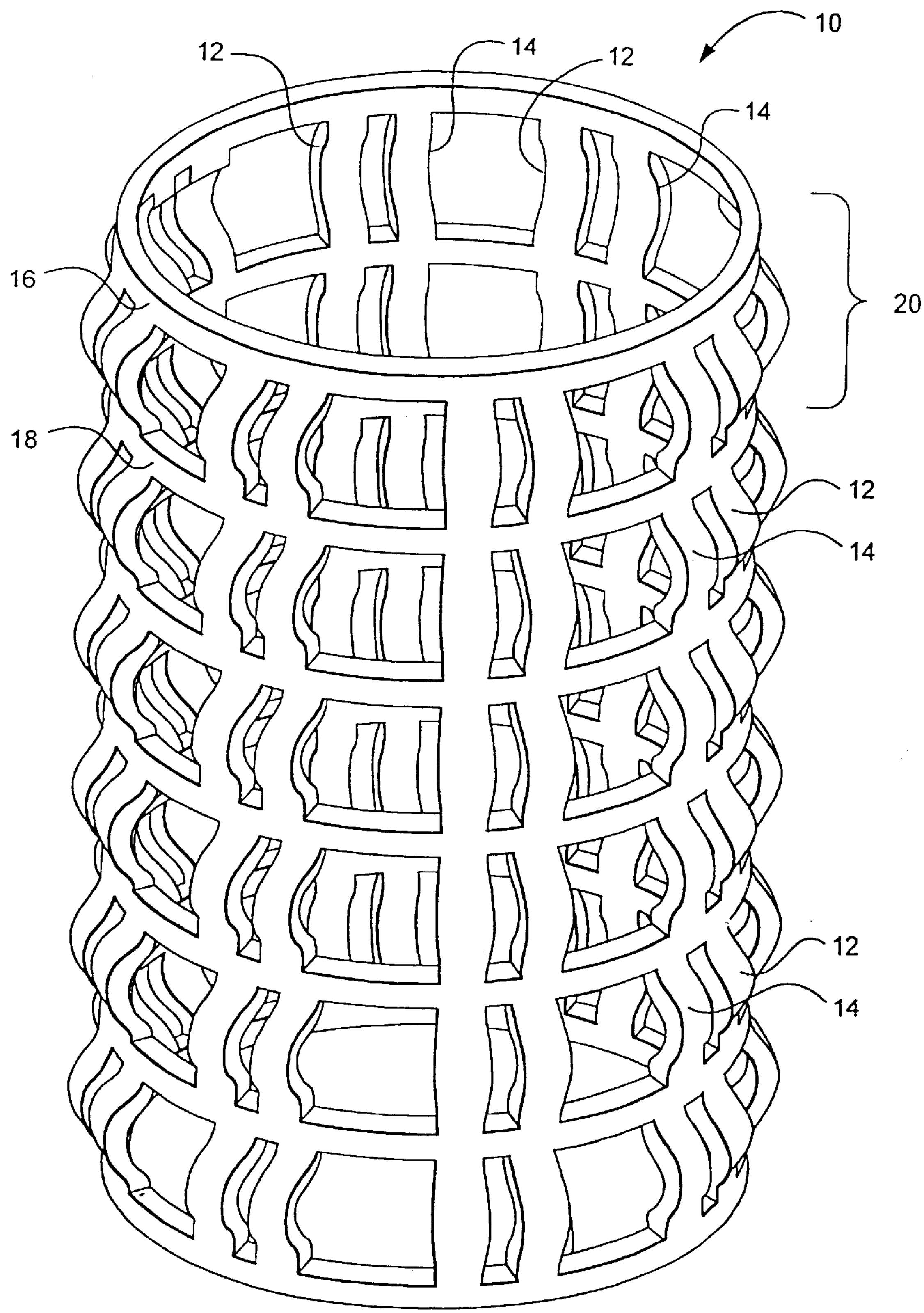
FIG. 1 is a perspective view of a thin-film shape memory alloy actuator array.

A shape memory alloy actuator array 10 formed in accordance with one aspect of the present invention is generally illustrated in FIG. 1. The shape memory alloy actuator array 10 may be formed from a plurality of individually trained shape memory alloy actuators 12 and 14 to provide relative movement of different array portions. The shape memory alloy actuators 12 and 14 may be positioned in between at least two connecting rings 16 and 18 which provide segmented joints within the actuator array 10. Each shape memory alloy actuator 12 may be adjacently positioned another actuator 14 along a different portion of the bordering connecting rings 16 and 18. The actuators 12 and 14 may be spaced apart along different portions along the connecting rings 16 and 18, or positioned in side by side pairs. When positioned in a side by side manner, each actuator pair may include oppositely trained actuators 12 and 14 so that one actuator 12 expands or extends towards a predetermined shape when heated, and one actuator 14 contracts towards a predetermined shape when heated. The total number of shape memory alloy actuators 12 that are trained to expand when activated may be equal to or different than the total number of shape memory alloy actuators 14 that are trained to contract when activated. The actuators 12 and 14 may be trained to expand or contract in opposition to other array actuators in what may be characterized as a push-pull relationship to provide relative movement of the array 10. Multiple stages or tiers 20 of actuators form an array of segmented joints that provide various actuator configurations.

As shown in FIG. 1, the segmented actuator array 10 may be formed with a substantially columnar configuration. The overall configuration of the array 10 may of course have different symmetrical or asymmetrical cross sectional shapes for various medical device applications. For example, the array may be formed for attachment to the distal portion of a guide or diagnostic catheter or any other portion of the device (not shown). In this manner, a distal catheter portion may be manipulated within various body cavities and blood vessels that are particularly difficult to reach without actuator assistance. The array 10 may also be formed into a steerable cuff that operates as an attachment or guide that achieves movement through a series of controlled contractions and expansions of array actuators. Alternatively, the shape memory alloy array 10 may be integrally formed with a catheter or instrument body. It may be further possible to combine a series of multiple arrays 10 together to provide independent movement of different portions along a catheter body. The actuator array 10 shown in FIG. 1 may be further modified to provide a stents device wherein selected actuators 12 and 14 are activated to either expand or contract resulting in a highly customized fit for a selected body region. The biocompatibility of many shape memory alloys further encourages the continued development for their use in many other medical devices including endoscopic apparatus.

Figure 2A:
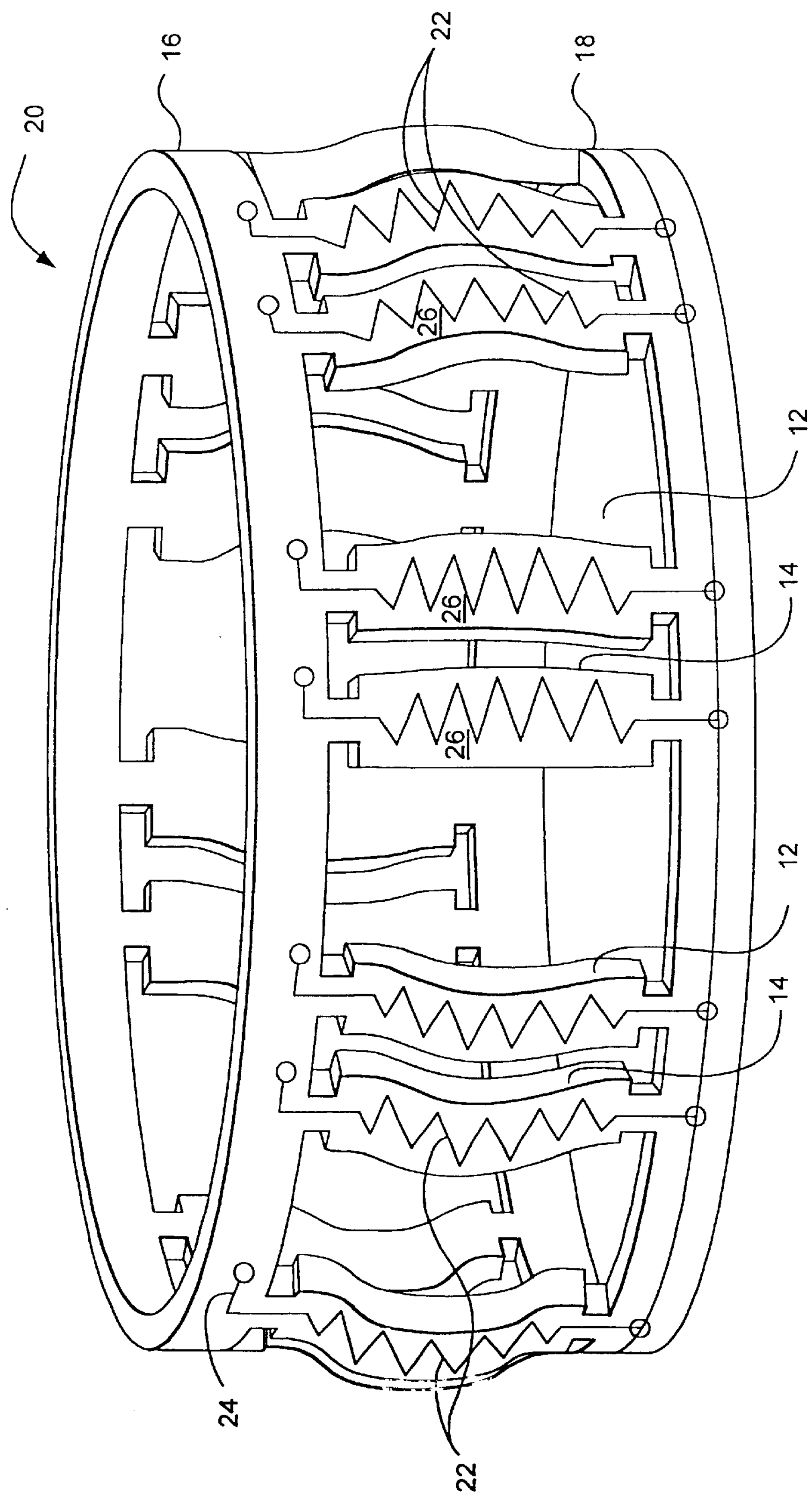
FIGS. 2A–2C are sectional perspective illustrations of different shape memory alloy actuators positioned between connecting rings.

As shown in FIG. 2A, an actuator array 10 may consist of a series of individual stages or tiers 20. Actuator pairs 12 and 14 may be circumferentially aligned in side by side pairs between common connecting rings 16 and 18 within each stage 20. The number of stages 20, and the number of actuator pairs 12 and 14 per stage, may of course vary depending on certain applications. Each respective actuator within each pair 12 and 14 is preferably formed with its own addressable thin-film heating element 22 which may thermally activate the individual actuator for movement away from its initial shape. In this manner, specific addressable thin-film heaters 22 may be activated for selected actuators 12 and 14 in order to alter ring-to-ring tilt angles within an actuator array 10. A heating element 22 may be of course positioned on either of the relatively inner or outer surfaces of the actuator array 10, or may be even embedded within the body of the actuator 12 itself. The activation of an actuator 12, which is preferably formed from a shape memory alloy, may be carried out by application of heat or any other activating stimulus. Current may be directed through heating elements 22 or resistance devices to selectively activate certain actuators 12 and 14 upon command. The wire leads 24 for the heating elements 22 of multiple actuators 12 and 14 may be connected to other actuators on the same stage 20, or other actuators located on other stages of the array 10, to form a network of thin-film heaters that controls movement of the array. In this manner, a relatively large number of actuators 12 and 14 within an array 10 may be easily networked and selectively activated by the application of a thin-film heating or activating system. The application of the thin-film heating network may be accomplished separately from, but in coordination with, the particular design and manufacture of the actuator array 10. Upon forming the desired actuator pattern from shape memory alloy, a complementary thin-film layer of separately addressable heating elements 22 may be superimposed and fixed on the actuator pattern prior to final product assembly. Heat may be applied to a relatively large surface portion of an actuator surface 26, and is not locally restricted to only one end or section of the actuator. Upon selective activation, an actuator 14 within any given pair may contract to provide a desired movement within the array 10 while its counterpart 12 may in turn expand to provide a countermovement to return the array back to its original position. The separately trained actuators 12 and 14 may therefore work in opposition to each other in order to achieve desired movement of the array 10.

Figure 2B:
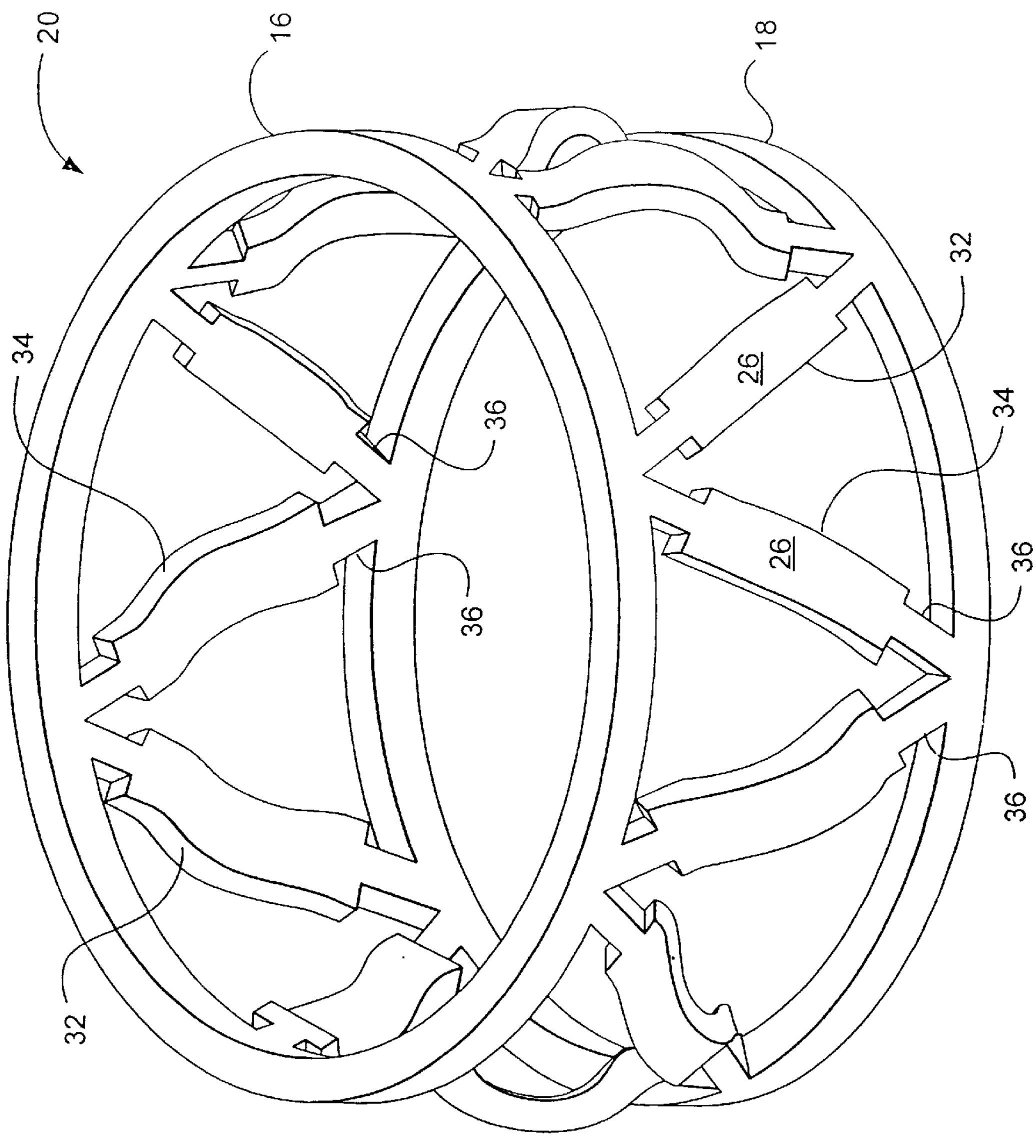
Figure 2C:
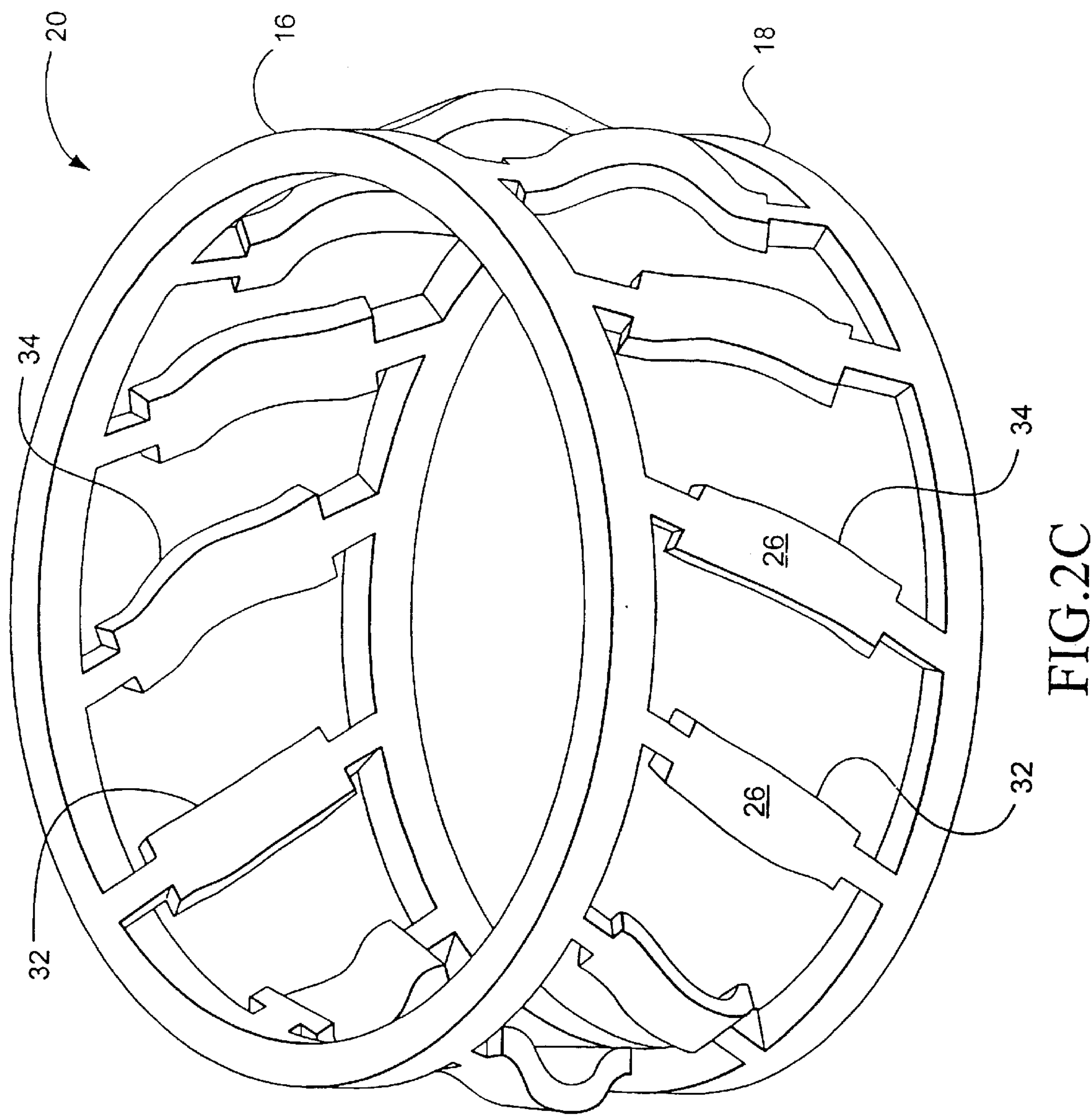

FIGS. 2B and 2C illustrate other embodiments of the invention that include angled actuator pairs 32 and 34 within any particular stage 20 of the actuator array 10. As s shown in these and other illustrations of the present invention, the end portions of the actuators 32 and 34 are preferably formed with notches 36. Although the body and end portions of an actuator 32 may have any configuration, these notches 36 have been observed to provide less restrictive movement during expansion or contraction of an actuator. A plurality of shape memory alloy actuators 32 and 34 may also be positioned at an angle in between connecting rings 16 and 18. The actuators 32 and 34 may be aligned so that actuator end portions are angled towards each other as shown in FIG. 2B, or in a parallel arrangement as shown in FIG. 2C. In either configuration, an actuator 32 may be provided to act in opposition to at least one other oppositely trained actuator 34. An actuator 32 may thus return to its originally trained shape with a biasing element 34. The biasing element 34 may be also formed of from a shape memory alloy, elastomer material, or other devices such as springs or piezoelectric or pneumatic elements that may be used to return an actuator to an initial configuration and dimension. For example, piezo elements may provide a biasing force in a selected direction when certain voltage is applied to the element. The actuators 32 and 34 may also be positioned at an angle to provide additional benefits offered by force amplification principles. A beneficial range of directional and rotational movement between adjacent connecting rings 16 and 18 may still be achieved with a reduced amount of contracting or expanding force. The actuator array stages 20 shown in FIGS. 2B and 2C may include expanding actuators 32 alternately positioned adjacent to contracting actuators 34. Similarly trained actuators may also be positioned in groups of two or more within a particular stage 20 of an actuator array. But an equal number of actuators 32 and 34 that are trained to expand and to contract within an array portion has been observed to provide a particularly well balanced range of movement. The number of oppositely trained actuators 32 and 34 between particular connecting rings or intermediary spacers 16 and 18 within the actuator array 10 may be of course dependent upon the desired range of movement and other variable parameters. The various positioning of actuators within intermediary spacers shown in preceding illustrations may form various combinations of multiple stage actuator arrays. While the illustrated embodiments throughout this description of the invention includes circular connecting rings 16 and 18, it is understood they may have different configurations. Medical devices are available in many sizes and shapes, and have different cross sectional configurations. An actuator array 10 may therefore include connecting rings 16 and 18 with a complementary geometry to form or to fit around these various devices.

For particular applications that require relatively small actuator assemblies, an actuator device may include a lattice network of individually configured shape memory alloy micro-actuators, and an addressable thin-film heater element in communication with the shape memory alloy portion for activation of selected micro-actuators. Multiple stages of micro-actuators may be separated with connecting rings described herein for separating the micro-actuators into segmented joints. At least one micro-actuator within a defined array section may be trained to expand upon heating by an addressable heater element, and at least one micro-actuator may be trained to contract upon heating by another addressable heater element. A selected combination of micro-actuators may be activated for varying the relative stiffness of the shape memory alloy portion. The micro-actuators may of course be arranged in any of the array configurations disclosed herein or any combination of the same. These miniature devices or micromachines tend to require relatively less energy to operate, and their design is preferably simple and permits fine adjustment and positioning.

Figure 3A:
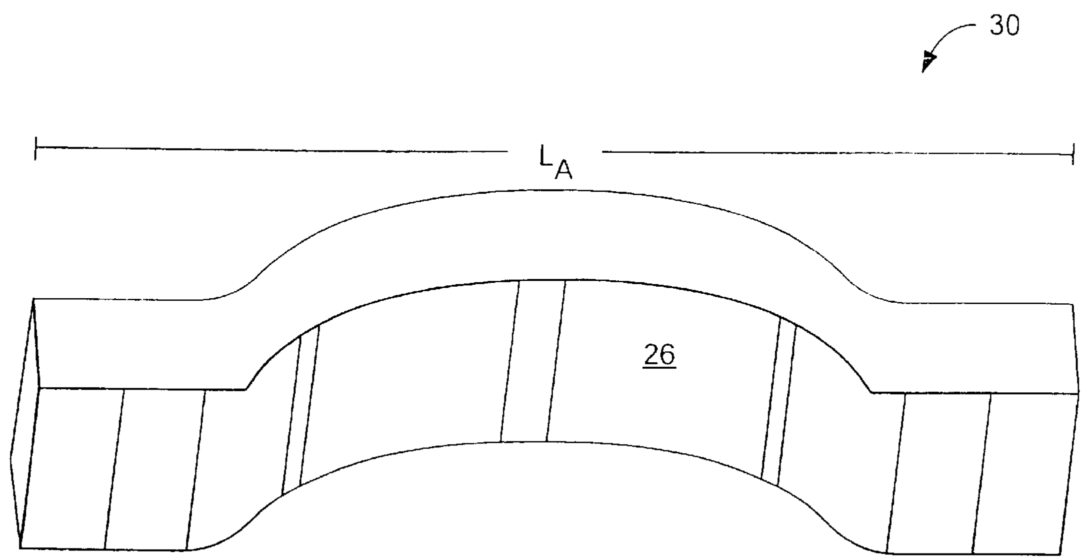
FIGS. 3A–3B are perspective views of a buckled actuator with an initial shape and a predetermined trained shape.
Figure 3B:
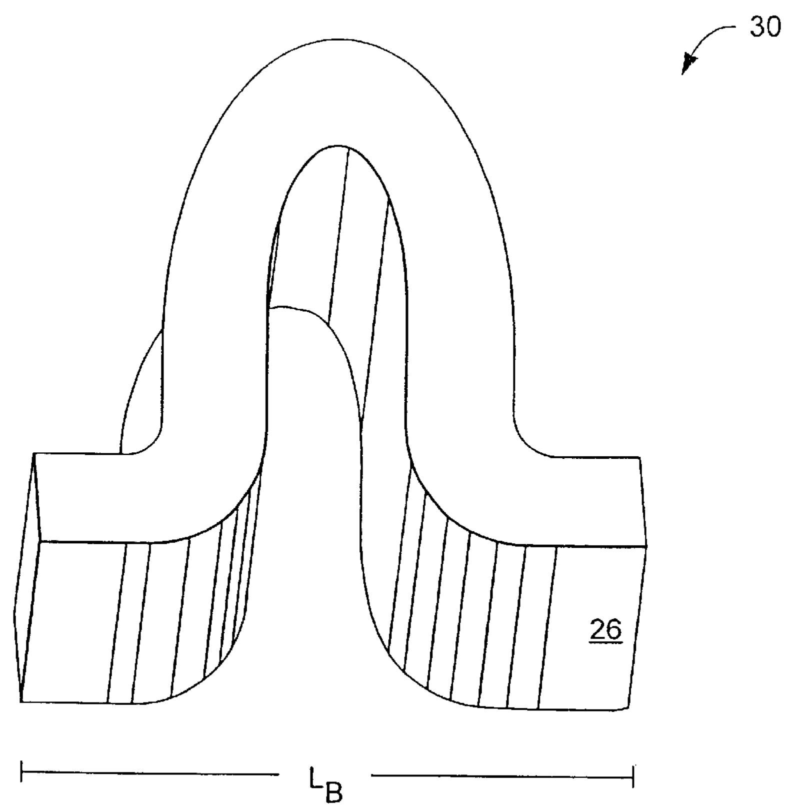

FIGS. 3A–3B illustrate a buckled actuator 30 with an initial shape and a trained predetermined shape. The actuator 30 may be trained with an extended configuration $L_A$ as shown in FIG. 3A to provide an actuator that expands when initially deformed and activated. Alternatively, an actuator 30 may be programmed with a contracted configuration $L_B$ as shown in FIG. 3B to provide an actuator that is trained to contract when initially lengthened. In any event, the buckled actuator 30 will move away from an initially deformed shape towards its predetermined shape when activated. Shape memory actuators such as those described herein provide a substantial and uniform force when fully constrained, or useful work when partially constrained or activated. Initially, shape memory alloys are easily deformable and flexible in their martensitic form, and become more stiff and inflexible when they revert back to their austenitic or parent form when heated. Although the actuators may of course have a wide variety of planar or nonplanar shapes including a helical, straight wire, corrugated or kinked pattern, the buckled configuration as shown in FIGS. 3A and 3B provides appreciable benefits. Actuators formed with an initial buckled shape provides efficient and useful work when moving towards its substantially planar predetermined shape. The amount of force needed to provide contracting or expanding movement is reduced by using a buckled actuator with an increased length. The buckled configuration exploits force amplification principles through bending movement as opposed to linear movement, and takes advantage of the extended length of the buckled actuator. An entire shape memory alloy array may be formed with actuators having this initial buckled or nonplanar shape and substantially planar predetermined shape.

Figure 4:
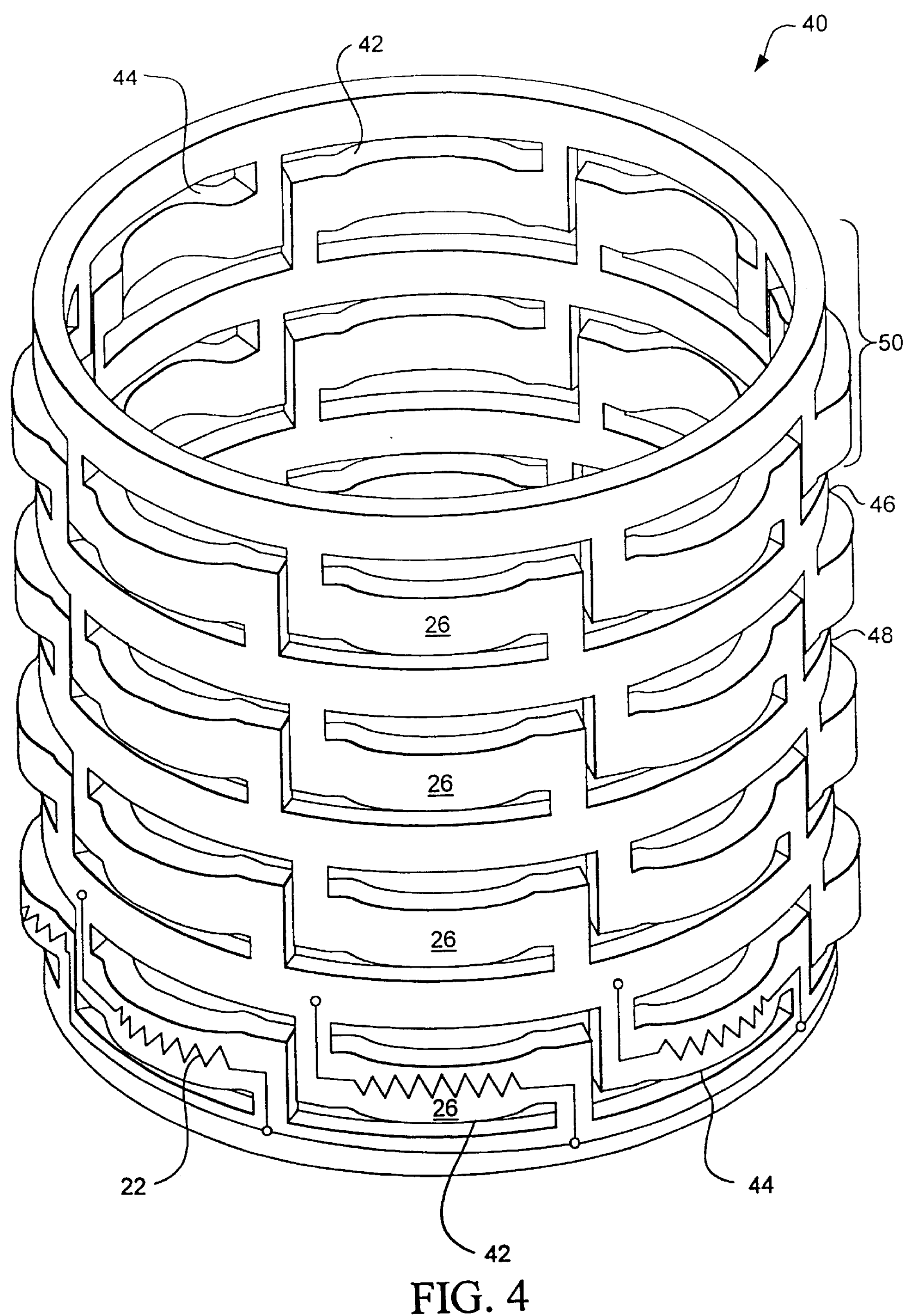
FIG. 4 is a perspective view of a thin-film shape memory alloy actuator array that provides rotational movement between relative array portions.

Another actuator assembly 40 formed in accordance with the concepts of the invention is illustrated in FIG. 4. The actuator scaffolding 40 shown in FIG. 4 may be particularly formed to provide rotational movement relative to the axis of the array 10. A portion of a medical device such as a catheter (not shown) may include a scaffolding 10 formed of individually addressable and activated shape memory alloy actuators 42 and 44 that are configured to provide a full range of directional movement within a body including rotational movement. At least one heating element 22, which may be similar to other thin-film heating elements and systems described herein, is in communication with the scaffolding surface 26 to selectively activate a combination of at least one actuator 42 towards a predetermined state. The scaffolding 40 may include at least two connecting rings 46 and 48 to support relative movement of the shape memory alloy medical device. The actuators 42 and 44 within the scaffolding 40 may include substantially rectangular configuration with a buckled surfaces 26 that are either longitudinally or laterally aligned relative to the scaffolding, or any combination thereof. A plurality of heating elements 22 may provide a system of separately addressable thin-film heaters that thermally activates a selected combination of at least one actuator 42 to vary the ring to ring tilt or rotational angle of the scaffolding 40 within a predetermined range. The heating elements 22 may thermally activate a selected combination of at least one trained actuator 42 towards an intermediate state, or a final trained state, for relative movement of the device within the body. In a preferable embodiment of the invention, as shown in FIG. 4, each laterally aligned actuator 42 and 44 within a scaffolding stage 50 may be alternately trained to expand or to contract when activated. The selective activation of every other similarly trained shape memory alloy actuator 42 may provide a clockwise or counterclockwise movement for that array portion relative to adjacent portions. A countermovement may be achieved by the subsequent activation of other oppositely trained actuators 44 within the scaffolding stage to provide rotational movement between relative array portions. As illustrated in FIG. 4, the actuator scaffolding 40 may consist of multiple stages or tiers 50 of actuators 42 and 44 that contract or expand when activated. While every other actuator 42 within each stage or tier may be alternately trained to either expand or contract to provide a rotational movement in a particular direction, stacking the multiple rotating stages or tiers 50 may amplify the net rotation of the overall scaffolding or array 40. The extent of rotational movement may either be determined in part by the change in length between the overall activated and non-activated actuator lengths, or the number of stages 50. As with all of the longitudinally, laterally or angled actuators illustrated herein, the relative sizes and dimensions of these elements may also be modified to provide the desired linear or rotational movement.

Figure 5:
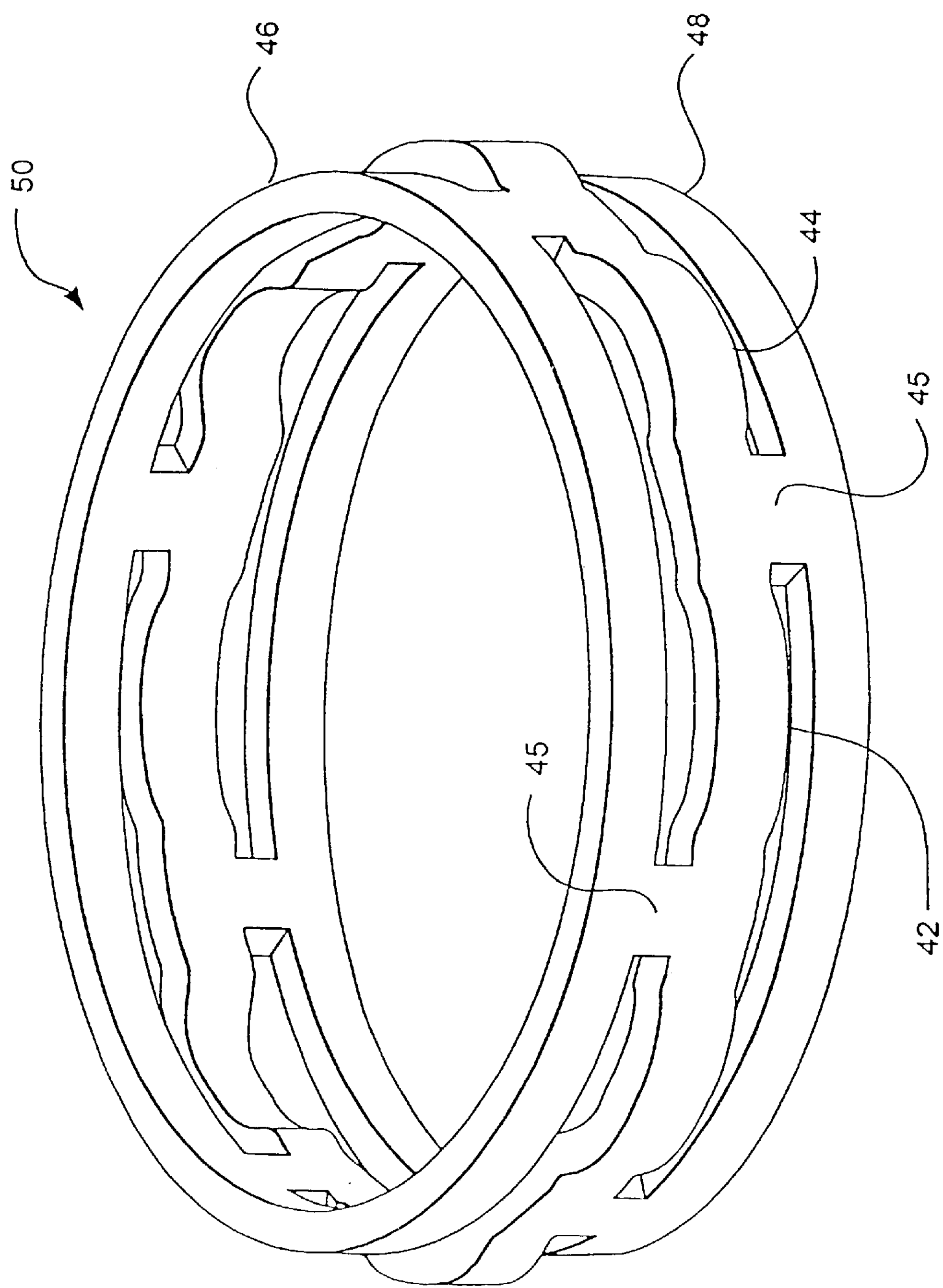
FIG. 5 is a sectional perspective view of shape memory alloy actuators positioned between connecting rings and actuator extensions to support relative rotational movement of the actuator array.

FIG. 5 illustrates yet another embodiment of the invention that includes shape memory alloy actuators 42 and 44 positioned in between connecting rings 46 and 48 and actuator extensions 45 to support relative rotational movement of the actuator array 10. Any of the aforementioned actuator configurations and stages may be combined to form the skeletal structure of a thermally activated directional actuator device. The skeletal structure formed with a plurality of intermediary spacers or connecting rings 46 and 48 for supporting relative movement of the directional actuator portions. The intermediary spacers 46 and 48 may further include actuator extensions 45 for connection to actuators positioned within a particular tier 50. Individual actuator extensions may be formed for connection to adjacent connecting rings at each end of an actuator, or alternatively, actuators may share a common actuator extension 45.

Any of the actuator portions described herein may be combined to form a variety of shape memory alloy devices. Actuators may be positioned in any combination of angled, lateral, or longitudinal orientations relative to the axis of the array. However, it is preferable that actuators within a specified stage of the array have a consistent predetermined orientation to provide a high degree of balanced actuator movement in all directions including linear and rotational movement. For example, a skeletal structure may be formed with at least two oblong actuators 12 and 14 longitudinally aligned relative to the structure, and at least two oblong actuators 42 and 44 laterally aligned relative to the structure for relative movement of the skeletal structure portion. A series of connecting rings 16 and 18 may be formed with actuator extensions 45 for connecting actuators 42 and 44 laterally aligned relative to the actuator device. The laterally aligned actuators may include at least one actuator 42 that expands in length when heated and at least one actuator 44 that contracts in length when heated. Because addressable thin-film heaters may be used to activate and control selected actuators, a large number of shape memory actuators may be included in the array to provide a full range of precise directional movement. As explained above, the extent of heating or activation provides both directional movement and a change in relative stiffness of actuator array portions. Selected heating of some or all actuators within the actuator array provides a shape memory alloy device with a wide range of controlled movement and variable stiffness. Other suitable materials with memory capability may also be used instead of shape memory alloy to provide similar actuator devices. A plurality of actuator arrays described herein may be further combined to form more complex structures to provide an even wider range of movement. Combinations of array portions may even be combined to form finger or hand-like projections, or any other mechanically useful configuration, to provide a full range of controlled movements.

Figure 6:
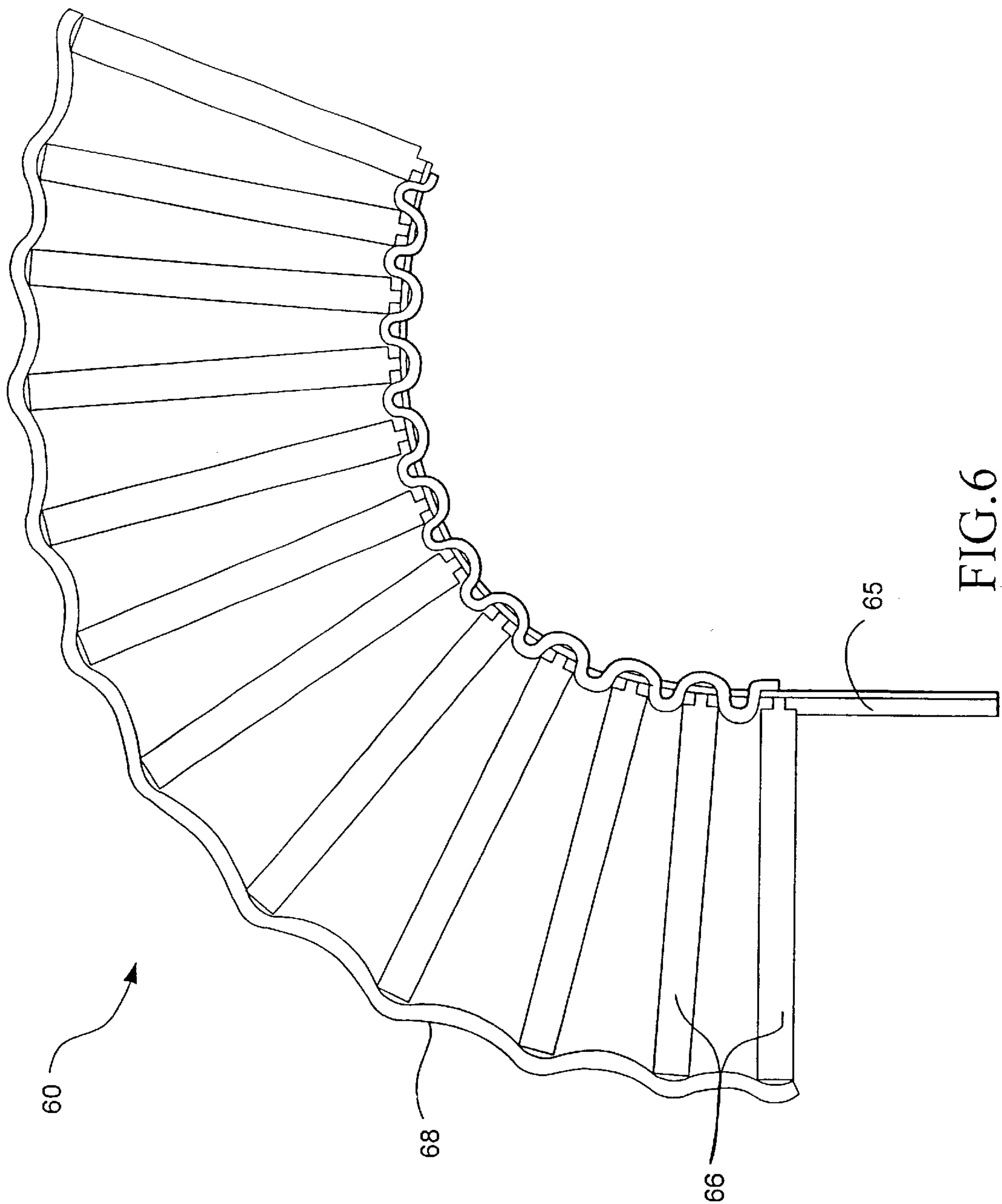
FIG. 6 is a side view of a thermally activated directional actuator device with a shape memory alloy skeletal structure and a polymer coated ribbed portion.
Figure 7:
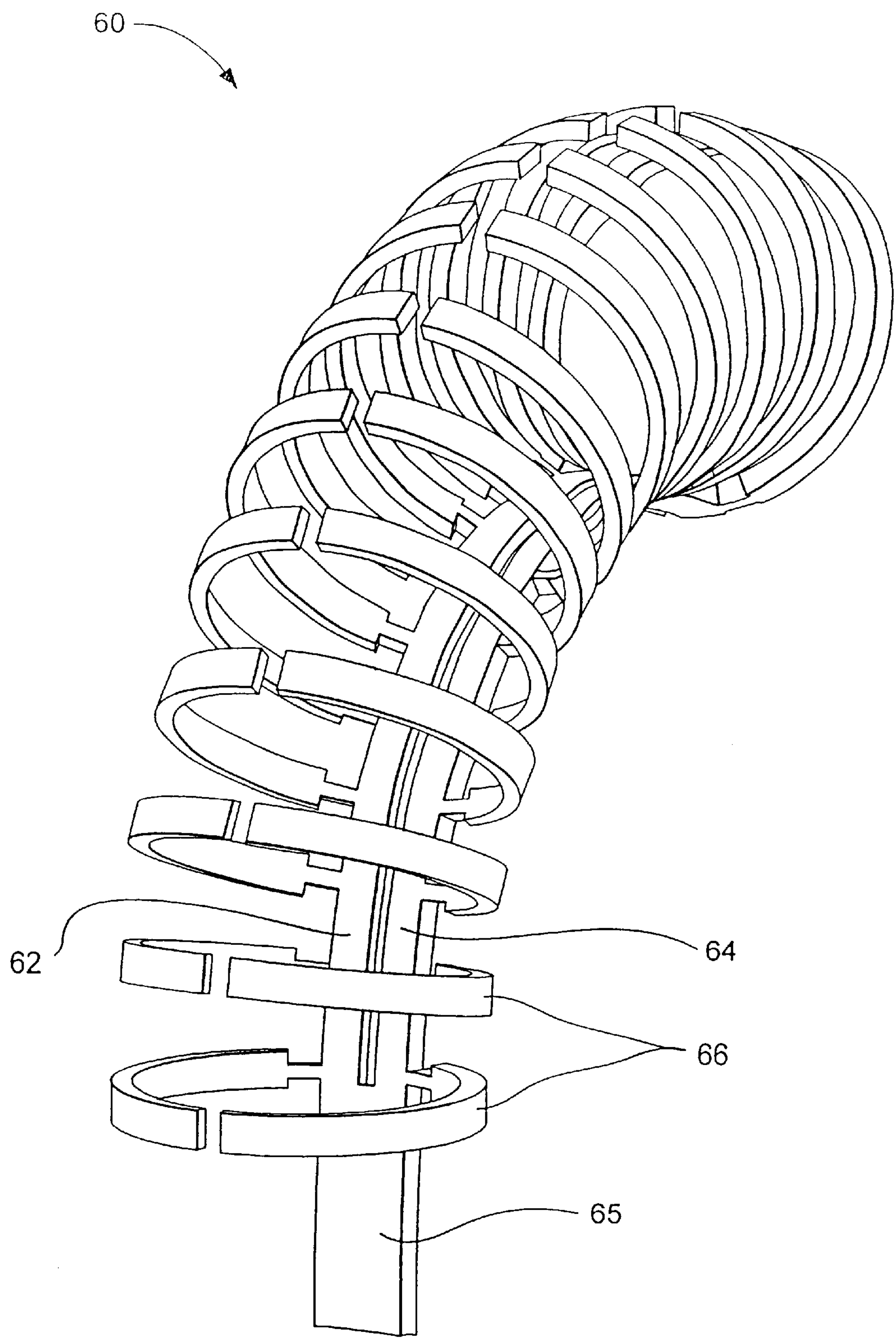
FIG. 7 is a perspective view of an actuator device similar to the embodiment illustrated in FIG. 6 capable of arcuate movement and bending of the shape memory alloy backbone structure.
Figure 8:
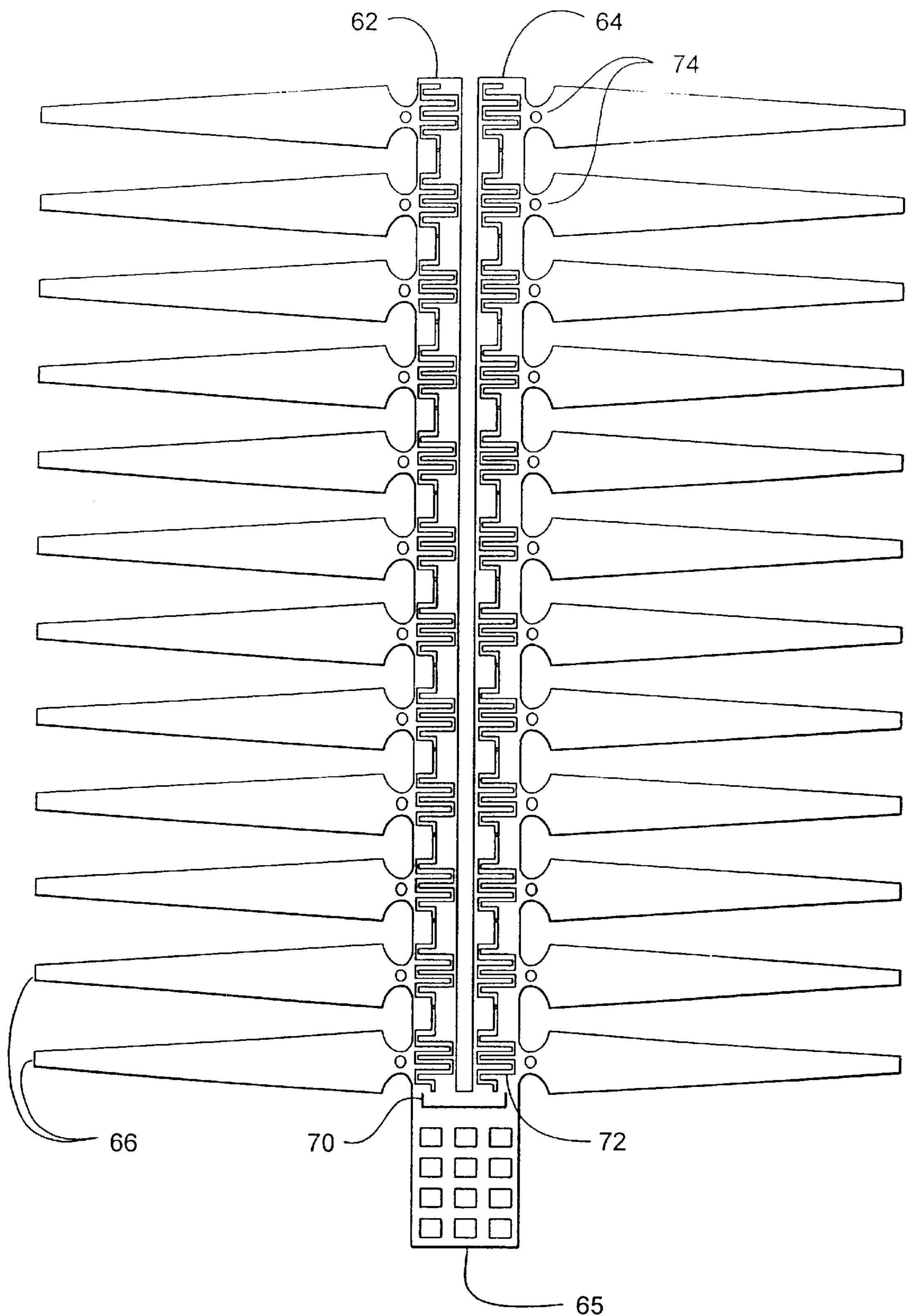
FIG. 8 is a front view of a layout for a thermally activated actuator similar to the embodiments shown in FIGS. 6 and 7 formed from a sheet of shape memory alloy.

A thermally activated directional actuator device formed in accordance with the concepts of present invention is similarly shown in FIGS. 6-8. The actuator device may comprise a shape memory alloy skeletal structure 60 with a series of ribbed portions 66 that are enclosed within a polymer coating 68. The skeletal structure 60 may also include a backbone 65 formed of two shape memory alloy actuators 62 and 64 configured with a predetermined shape, and a heating system 70 having individual localized heaters 72 for moving each actuator towards its predetermined shape. An actuator portion 64 of the shape memory alloy backbone may contract when thermally activated while another backbone portion 62 may expand or extend when thermally activated to provide arcuate movement of the actuator device. The skeletal structure 60 may also include a ribbed cage section 66 formed along the backbone portion 65. The ribbed cage section 66 may also include shape memory alloy rib portions of various shapes, and may be activated by separately addressable thin-film heaters (not shown). As with other actuator arrays described herein, the ribbed cage section 66 may be particularly formed to support the distal portion of a catheter body. In addition, portions of the directional actuator 60 may be encapsulated within one or more polymer coatings 68. A separate polymer coating may support thin-film heating elements 72 along selected portions of the skeletal structure 60. As with other actuator arrays described herein, the embodiment shown in FIG. 6 may include a pair of oppositely trained shape memory alloy actuators 62 and 64 that provide movement and countermovements relative to each other. The full range of movement between the initial deformed shape of an actuator and its predetermined shape includes various intermediates shapes that provide useful work and directed motion. FIG. 8 provides an illustration of a pattern layout for a similar actuator device shown in FIGS. 6–7 that may be formed from a single sheet of shape memory alloy. A variety of sensor transducers, or a combination of both, may be included along various portions of the shape memory alloy structure 60 such as in the proximity of the heating elements 72.

As shown in FIGS. 7–8, the actuator device 60 may be designed to provide arcuate movement or bending motion within a shape memory alloy skeletal backbone structure 65. The steerable actuator array 60 may be used as a catheter cuff, and may be mounted onto an existing catheter at its distal tip or any other portion of the device. A wide variety of optical, pressure, temperature or any other type of sensing or transducer device, may be further included on a portion of the steerable device. Alternatively, the skeletal structure 60 itself may be integrally formed as the shape memory alloy section of a steerable device such as an endoscope or a catheter. The relative stiffness of selected or entire portions of the shape memory alloy devices described herein may also be varied by heating or activating a selected number actuators for their transformation to a relatively rigid austenitic state, while other inactivated actuators may be left in their relatively flexible martensitic state. For example, devices such as guide catheters and wires often require a certain degree of both stiffness and flexibility for traversing the various pathways within the body. While the device must exhibit good torque control and stiffness to resist undesired kinks and respond to maneuvering forces within narrow passageways such as blood vessels, catheters must also be flexible enough to pass through these areas without significant trauma to the surrounding area. The catheter may include a body portion formed entirely of a shape memory alloy, or at least a section that is adjacent to a catheter sidewall portion preferably formed of biocompatible polymeric material. The shape memory alloy section may have a skeletal structure configuration or any combination of the aforementioned actuator arrays.

Figure 9:
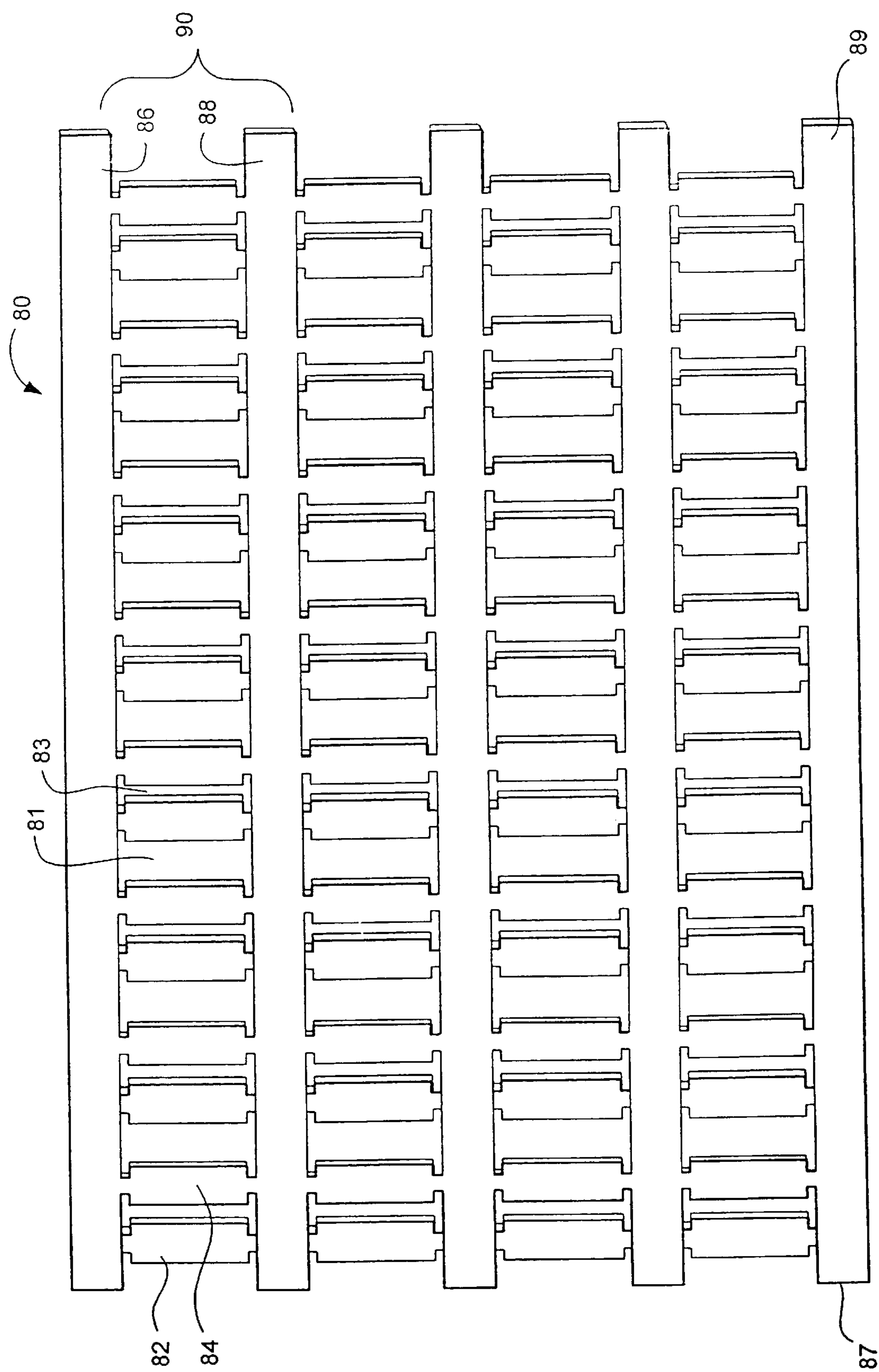
FIG. 9 is a perspective view of a pattern layout of a shape memory alloy actuator device that provides a plurality of shape memory alloy actuators formed by removing selected window portions of the sheet along a series of spaced apart rows and columns.

Another aspect of the present invention includes various methods of manufacturing and forming extremely maneuverable shape memory alloy actuator assemblies. Although any of the enclosed embodiments may be formed from a plurality of separate shape memory alloy sheets or pieces, it is particularly convenient and efficient to form these actuator devices from a single sheet of suitable material. FIG. 9 provides an illustrative example of a pattern layout for an actuator device that includes a plurality of shape memory alloy actuators 82 and 84 formed by removing selected window portions 81 and 83 of a single sheet of shape memory alloy 80 along a series of spaced apart rows and columns. A shape memory alloy actuator device may be constructed by initially selecting a sheet of shape memory alloy material 80 defined by at least two side edges 87 and 89, and forming a plurality of shape memory alloy actuators 82 and 84 to provide relative movement of the actuator by removing selected window portions 81 and 83 of the sheet along a series of spaced apart rows and columns as illustrated in FIG. 9. The shape memory alloy actuators 82 and 84 may be individually trained to a predetermined state prior to laying out a network of addressable heating elements provided on a thin-film sheet (not shown) that selectively activates the shape memory alloy actuators. The side edges 87 and 89 of the combined heater elements and shape memory alloy sheets may be finally sealed to form the actuator array.

The actuator array 10 may be formed from a single or multiple tiers 90 that consist of two connecting rings and a series of shape memory alloy actuators. The actuator rows may be sufficiently spaced apart to form connecting rings 86 and 88 to support relative movement of the shape memory alloy actuator array 10. The actuator columns may also be spaced apart to generally define the lateral portions of the shape memory alloy actuators 82 and 84. Selected window portions 81 and 83 may be removed from the shape memory alloy sheet 80 to form the individual actuators 82 and 84. The window portions 81 and 83 may of course vary in shape and size according to the desired configuration of individual actuators 82 and 84 and the overall array 10. In the particular embodiment shown in FIG. 9, selected large 81 and small 83 "I-shaped" portions are alternately removed from the single sheet 80 to provide a plurality of notched shape memory alloy actuators 82 and 84 formed in side by side pairs. Larger removed portions 81 provide spacing between actuator pairs, while smaller removed portions 83 separate individual actuators within each pair. The actuators 82 and 84 may be trained before or after they are formed from the sheet of shape memory alloy 80 or similar material with memory capabilities. Although it may be preferable to train the individual actuators 82 and 84 before laying out thin-film heaters (not shown) on the sheet of shape memory alloy 80, it may be desirable to first combine the sheet of shape memory alloy and heater before forming and training the actuators.

Shape memory alloy actuators may be individually or collectively trained to move towards a predetermined shape by heating or activation. Shape setting may be accomplished by constraining an NiTi element on a wire, mandrel or fixture of any desired shape, during appropriate heat treatment. The heat treatment parameters chosen to set both the shape and the properties of a shape memory alloy element are often determined experimentally for specific applications. In general, a predetermined shape may be set at temperatures as low as 400° C. for approximately 1–2 minutes, or at temperatures closer to 500° C. to 800° C. for 5 minutes or even longer periods of time. A shape memory alloy element may be mechanically stressed at these elevated temperatures to form the desired trained configuration. While higher heat treatment times and temperatures have been observed to increase the actuation temperatures of the shape memory alloy component and limit their resultant peak forces, they often provide a sharper thermal response. Rapid cooling typically completes the training process with a water quench or application of rapid cool air which is particularly suitable when setting parts in fixtures that are relatively small. The training procedures described herein are merely examples of setting shape memory alloy components, and other well known training methods and apparatus may be similarly applied to the present invention. For example, actuators 84 that are trained to contract when activated may be positioned within a heating fixture with a concave portion that may run along and in between the rows of actuators. Actuators 82 that are trained to expand when activated may be positioned onto a heating fixture with a mandrel or wire portion that may similarly run along and in between the rows of actuators. An individual actuator 82 within each row of actuator pairs contained within the pattern illustrated in FIG. 9, for example, may be trained to expand. Similarly, the complementary actuator 84 within each pair may be trained to contract. Multiple rows or columns may also be simultaneously trained with suitable heating fixtures that may be modified by known methods. The training process described herein may set a relatively large number of actuators 82 and 84 in an efficient and time saving manner. Upon training and cooling of the actuator array pattern, the flexible actuators 82 and 84 may be deformed, or mechanically stressed, to a buckled configuration or any other convenient shape while the thin-film heating network (not shown) is applied. The edges 87 and 89 of the single array sheet 80 shown in FIG. 9 may be eventually sealed to form a shape memory alloy actuator tube similar to the device shown in FIG. 1. When an actuator 82 within the array is selectively heated to an elevated temperature, the internal structure of the shape memory alloy begins to change from a martensitic phase to a austenitic phase at a temperature referred to as (As) until it is complete at yet a higher temperature identified as (Af). During this process, the actuator recovers its original trained shape while producing a substantial resultant force. Upon cooling, the material begins to revert back to the more deformable martensitic state at a temperature referred to as (Ms) until the transformation is complete at a lower temperature known as (Mf). The temperature ranges for these phase transformations vary greatly with the particular composition of a shape memory alloy. Actuation temperatures of NiTi, for example, may be adjusted to precisely activate the material in the proximity of commonly required temperatures such as body temperature. When selecting and training shape memory alloys for medical device applications, these ranges are preferably within a tolerable limit or not too far removed from body temperature. Although the actuator patterns described herein are particularly suited for single sheet construction and training, any array configuration may be formed and appropriately trained with the disclosed concepts from multiple sheets of memory retentive material.

It should be noted that the actuator array configurations described herein may be formed from either one-way or two-way shape memory alloys. One-way alloys have a single high temperature trained shape. Two-way alloys have both a low and high temperature configuration. While two-way alloys provide useful benefits in certain applications, one-way shape memory alloys generally require less complicated training methods and possess a significantly higher amounts of recoverable strain (6–8%) than two-way alloys (2%). Among other limitations attributed to two-way alloys, their transformation forces upon cooling are also relatively low. It has therefore been recognized that devices preferably include one-way shape memory alloys and a biasing force acting against the shape memory alloy element to return it to an initial deformed shape upon cooling. As described above, many biasing elements may be used with the shape memory actuators disclosed herein including springs, elastomers and another oppositely trained shape memory alloy actuator. A first actuator may be subjected to thermal treatment and trained so that its length is extended by a predetermined amount during a heating process from a low temperature to a high temperature. At the same time, a second actuator may be trained so that its length is reduced or compressed when activated. These oppositely trained actuators may be positioned within intermediary spacers described herein to provide a full range of linear and rotational movement for an actuator array.

Figure 10:
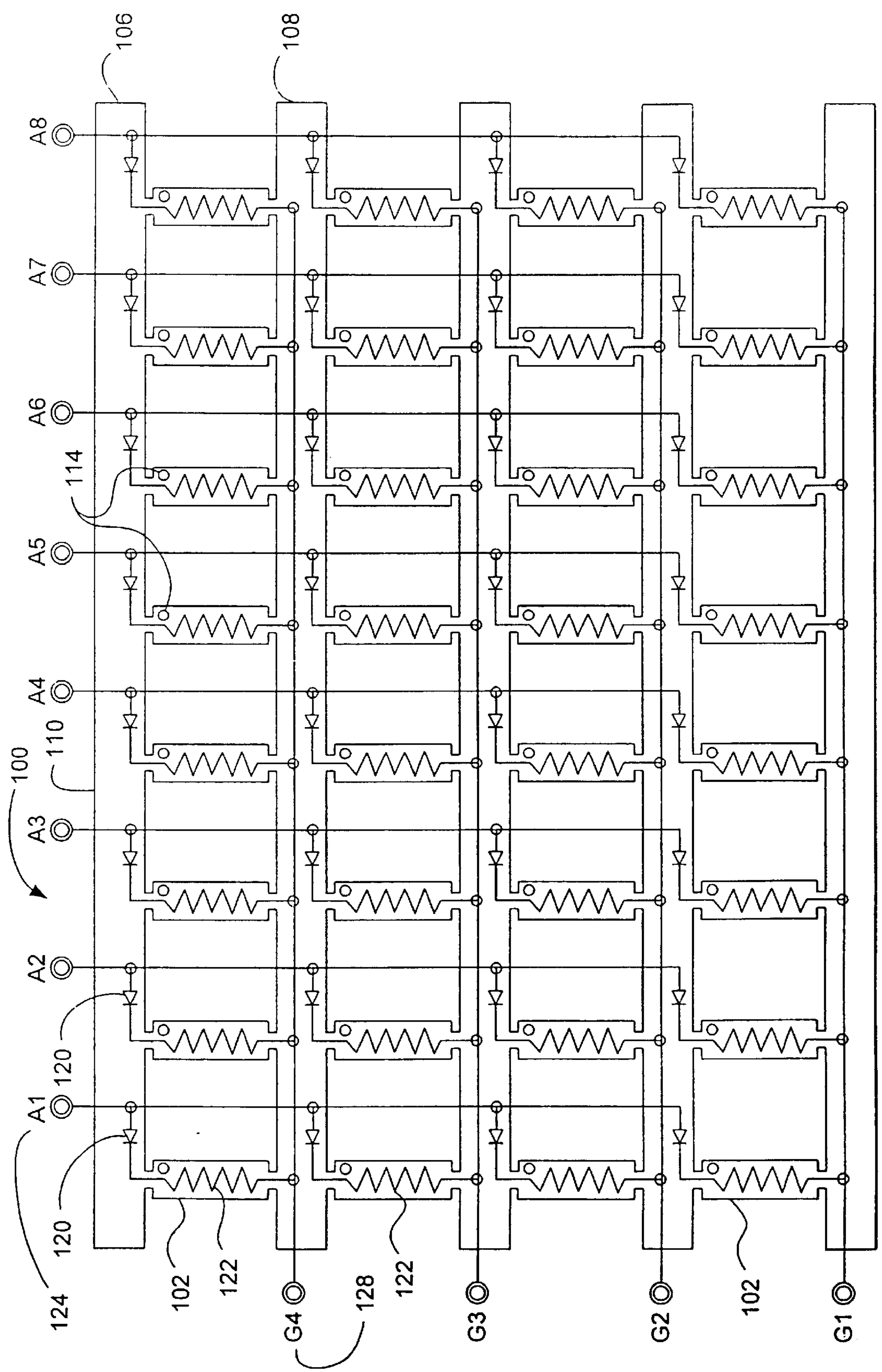
FIG. 10 is a front view schematic diagram illustrating a thin-film heating system deposited on a single pre-formed sheet of shape memory alloy material.

While one aspect of the present invention may be directed to the movement and countermovement provided by oppositely trained actuators within an actuator array, other concepts described herein provide an addressable system of thin-film heating elements. As shown in FIG. 10, a thin-film heating system 100 may be deposited on a single pre-formed sheet of shape memory alloy material 110. After an actuator array pattern is formed on the shape memory alloy sheet 110, a complementary thin-film sheet of heaters 122 may also be added. As described above, the actuator pattern may be alternatively formed after both sheets are joined. The design and application of a network of thin-film heaters 100 provides significant flexibility in the design of relatively complex or intricate shape memory alloy actuator arrays. A large number of actuators 102 formed with any shape or design may be selectively activated with adjoining addressable thin-film heating elements 122 which do not significantly add to the weight or size of the array. The shape memory alloy actuators 102 may be effectively heated over a relatively wide exposed surface area 126 to move the actuators 102 towards their trained shape in a particularly controlled and programmed manner. In FIG. 10, the addressable heaters 122 are wired or connected as part of a complete heater network 100. Current is supplied through a system of lead wires 124 leading to heating elements 122 positioned adjacent to each actuator within the array for activation. While an entire column or row of actuators may share a common heater line 124, each heater 122 is separately addressable and may be selectively activated. The installation of diodes 120 for multiple actuator heaters as shown in FIG. 10 further provide for the selective activation of specific heaters without incidentally affecting other actuator heaters 122 within the array. However, direct wires leading to each heater without diodes may similarly be used when some reverse flow of current may be acceptable. The actuator heaters 122 may further include resistors or other types of heat transfer elements to activate their respective shape memory alloy actuators 102. It has been observed that an optimal number of address lines may be achieved for arrangements where the number of actuators in each row are equal to, or nearly equal to, the number of actuators in each column. In this manner, an excess number of address lines are avoided while similarly avoiding the difficulty in controlling a relatively large number of heaters on a relatively few number of address lines. The thin-film heating network 100 may of course include any number of address lines and any number of addressable heaters for each address line. Ground wires 128 may be further provided for each row or column to complete the thin-film heater circuit 100. The ground wires 128 may run along the connecting rings or intermediary spacers 106 and 108 formed between formed actuators 102 in the array pattern. In addition, a variety of sensors, transducers 114, or both, may be included in the actuator array pattern to provide feedback on movement or surrounding conditions. Bending or deflection sensors 114 may provide signals indicating the relative positioning of actuator array portions such as strain gauges or piezoresistive elements. Other sensors that may assist in imaging techniques and similar procedures include electrochemical, electromagnetic, electropotential, hall effect, chemical or pH sensors. Similarly, the array may include various transducers that generate acoustic output signals or other useful emissions. Any combination of input and output devices may be positioned throughout the actuator array to provide desirable measurements and positioning information.

The network of addressable heating elements, sensors, and transducers may also be controlled and connected to a microprocessor control unit (not shown) for selectively activating a combination of at least one shape memory alloy actuator for relative movement of the actuator array. The array may form a section of a shape memory alloy conduit having a lattice structure formed of shape memory alloy micro-actuators and a network of heating elements formed about the lattice structure for activating selected shape memory actuators within the lattice structure. The network of heating elements may activate a selected combination of at least one actuator in the conduit to provide relative movement between conduit portions or vary the relative stiffness of lattice structure portions. The lattice structure may further include connecting rings with intermediary shape memory alloy micro-actuators that expand or contract when heated. The network of heating elements may be thin-film addressable heating elements controlled by a microprocessor unit that selectively activates a combination of at least one micro-actuator for relative movement of the shape memory alloy conduit or variable stiffness.

Figure 11:
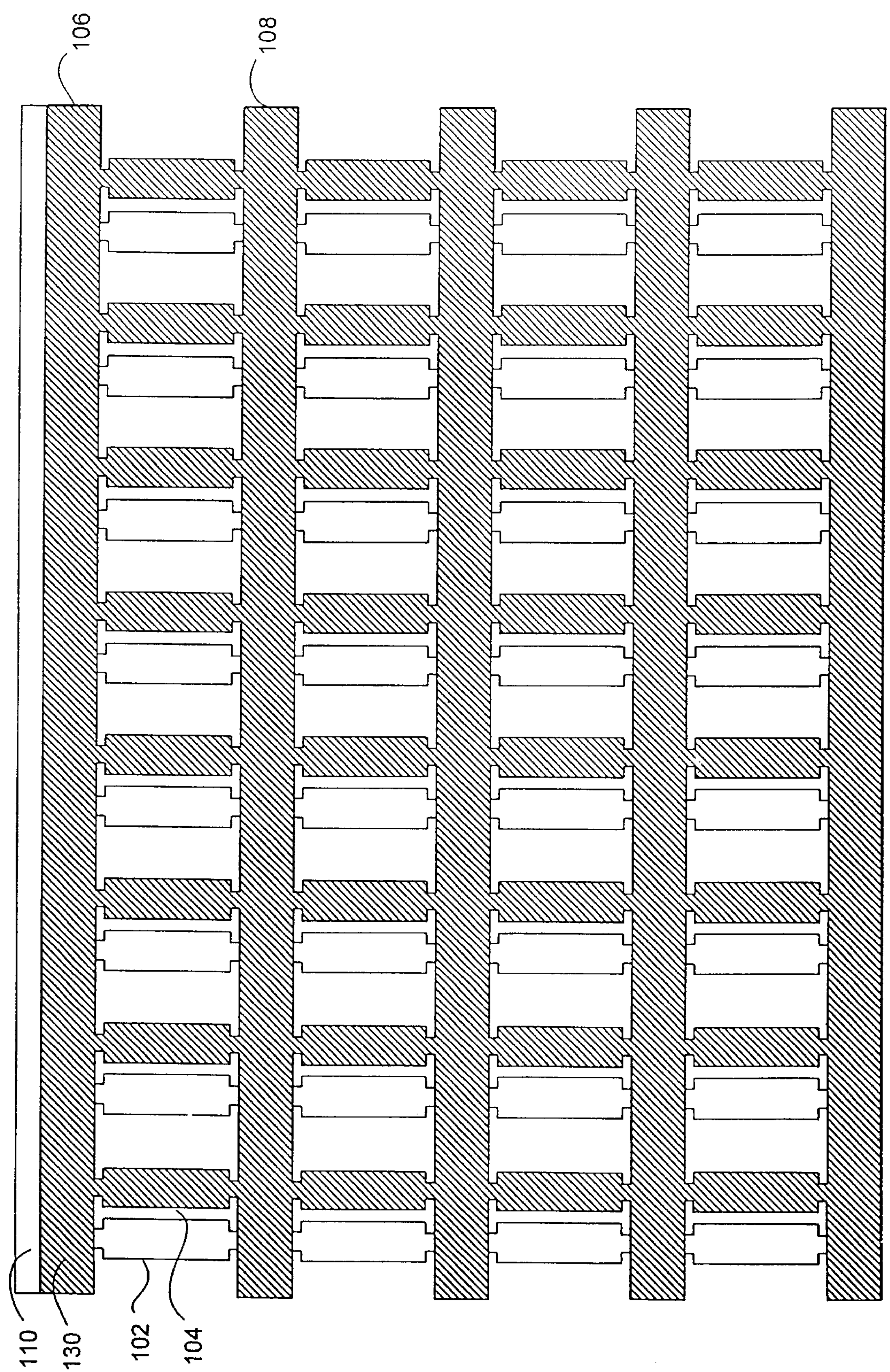
FIG. 11 is a front view of a pattern layout for an actuator device formed of two separate overlapping sheets of shape memory alloy that may include separately trained actuators that expand or contract when heat activated.

FIGS. 10 and 11 illustrate another variation of the present invention that provides for the manufacture of a shape memory alloy actuator array with two separately trained sheets 110 and 130. As shown in FIG. 11, an actuator device may also be formed of two or more separate overlapping sheets of shape memory alloy 110 and 130 that may include separately trained actuators 102 and 104 that either expand or contract when heat activated. Each of these sheets may include a separate thin-film heater network 100 or a combined heating system. The separate manufacturing of each sheet of shape memory alloy 110 and 130 may assist in the training process of the actuators 102 and 104. For example, all actuators 102 formed on the same sheet 110 may be trained in the same manner to either expand or to contract when activated. As described above, single or multiple heating fixtures may simultaneously train entire rows or columns of actuators. An additional sheet 130 of shape memory alloy actuators 104 may be separately and oppositely trained to complete the actuator array pattern. FIG. 11 illustrates overlapping and offsetting sheets 110 and 130 of shape memory alloy pattern similarly shown in FIG. 10. A final actuator array may be formed by welding or otherwise joining edges of the array pattern by known methods in the art.

Figure 12A:
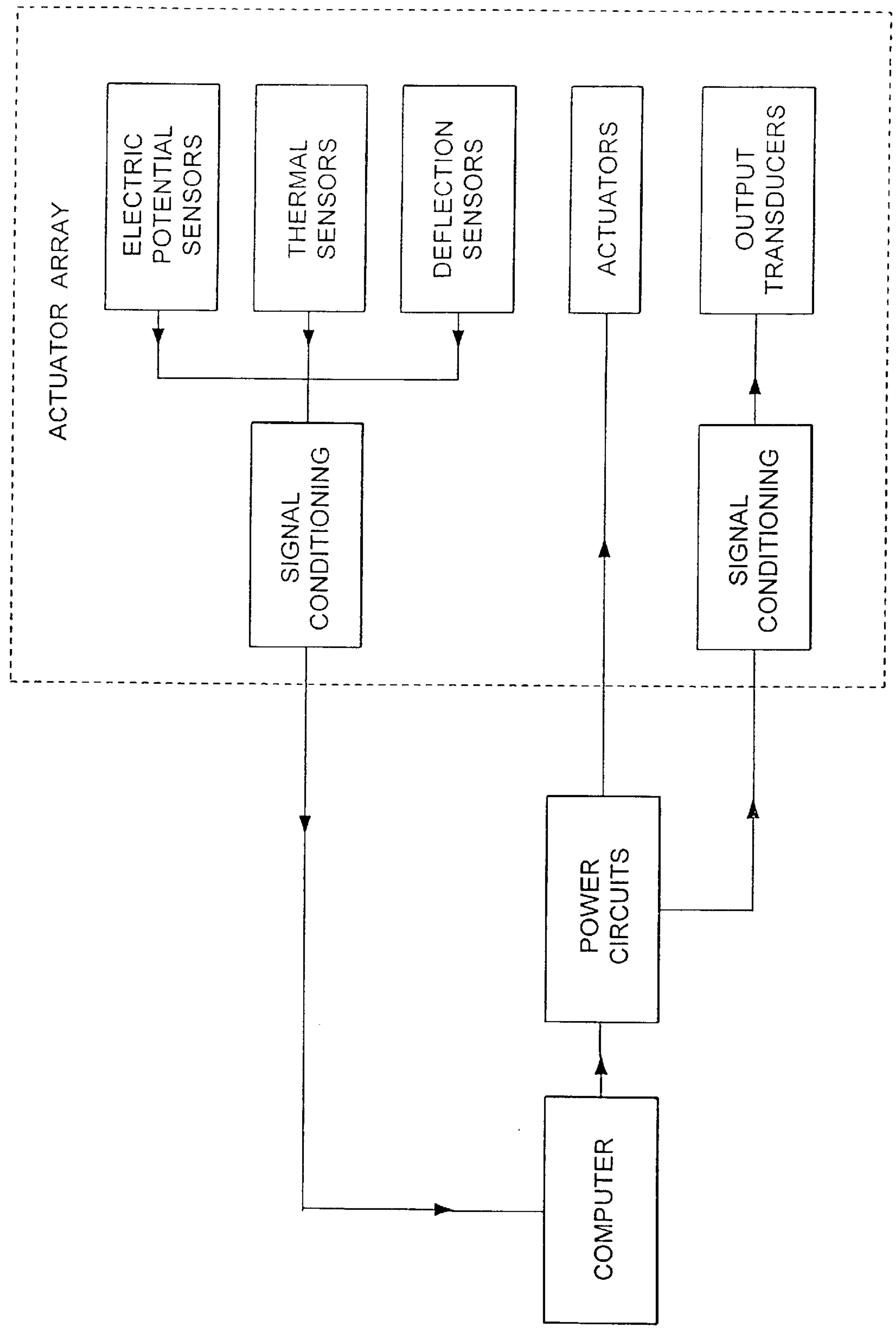
FIGS. 12A–B are simplified block diagrams illustrating the control mechanism for operating a network of separately addressable activators within a shape memory alloy array.
Figure 12B:
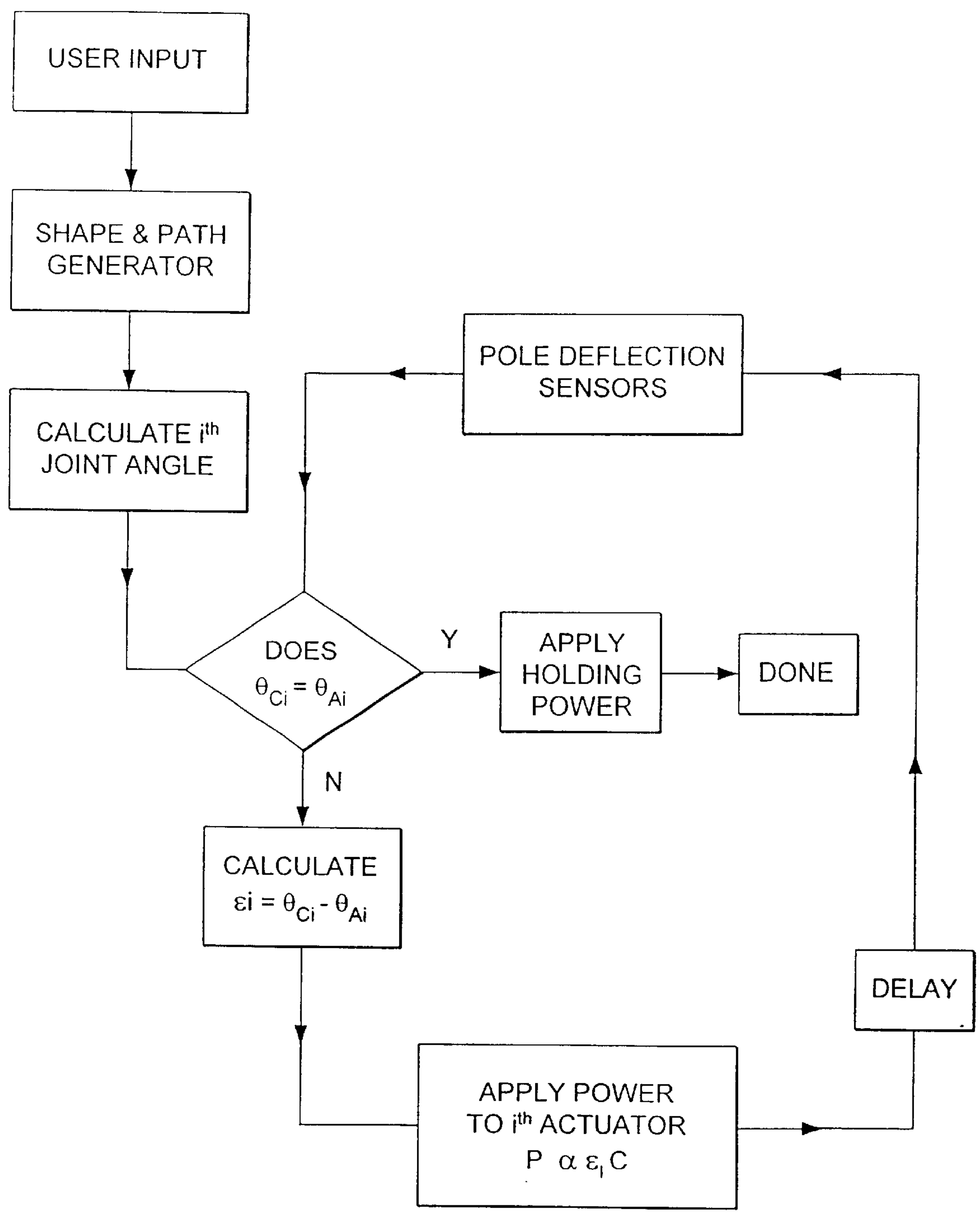

FIGS. 12A–B are simplified control flow diagrams for operating actuator arrays that may be formed in accordance with the invention. It should be understood that other control activation systems may be adapted for the actuator devices and systems described herein. As shown in FIG. 12A, a computer controls the movement or activation of any number of actuators within the array, and may direct and receive feedback from the array through a variety of sensors and transducers. While the described arrangement provides closed loop feedback information, the control and monitoring system may be configured as an open loop system by reconfiguring the sensor and output layout accordingly. A network of addressable heating elements, sensors, and transducers may be controlled and connected to a microprocessor control unit for selective activation and monitoring of a shape memory alloy actuator array. Various combinations of at least one actuator may be activated to provide relative movement between sections of the array or to vary the relative stiffness of selected array portions. The actuators may be activated with thin-film addressable heating elements controlled by the microprocessor unit.

Although other arrangements of these basic components may be selected, the illustrated computer is connected to power circuits that transmits command signals to the actuators and output transducers. The signals may be conditioned accordingly before reaching output transducers within the array, and may undergo amplification, filtering or any other desired conditioning. A variety of sensors may be positioned along various portions of the actuator array to provide relevant information on actuator activity, surrounding conditions or any other selected parameter. For example, optical, pressure, temperature or any other types of sensing or transducer devices, may be included on a portion of a shape memory alloy array that is configured as a steerable catheter or portion thereof The array sensors and transducers provide feedback on the relative movement of the array, and existing conditions within the array or its surroundings. Bending or deflection sensors may provide information relating to the positioning of actuator array portions, and may include devices such as strain gauges or piezoresistive elements. Other sensors that may assist in imaging techniques and similar procedures include electrochemical, electromagnetic, electric potential, thermal, hall effect, chemical or pH sensors. The array may also include various output transducers that generate acoustic signals or other useful emissions. Any combination of input and output devices may be therefore positioned throughout the actuator array to provide desirable measurements and relative positioning information.

In FIG. 12B, a simplified control flow diagram is provided that generally describes the method of activating and monitoring the movement of selected array portions. When a desired movement is elected, that request is entered into the control system as user input. This information may be simply provided as instructions to a microprocessor unit directly or may be derived from an additional peripheral device such as a joystick or any other directional steering mechanism. Upon entering the selected shape and desired movement of an actuator array, the resultant information is segmented or broken up according to particular regions or segments of the actuator array by a shape and path generator. Based upon the desired configuration and movement, selected joints within various segments of the array will be activated. At least one actuator may be provided for effecting movement of each joint within the array. A comparison is continually executed between the measured or actual joint angle for a corresponding actuator to determine whether the desired angle is achieved. A simple boolean comparison will either activate or hold the actuator in a desired configuration. When the calculated angle is different than the measured angle of the selected actuator, that difference is calculated. A variable amount of power is provided to the actuator by activating the actuator with a controlled heating component such as separately adjustable thin-film heating element. An entire network of thin-film heating elements may provide controlled activation and movement of an entire shape memory alloy actuator array. The power required to activate the actuator, and the extent to which the selected actuator moves or bends, is directly proportional to the difference between the desired and actual angles of the joint. An additional waiting period or delay may be added to the process in order to permit activation to occur before resultant movement of array is measured by pole deflection sensors. When the actual joint angle is achieved and equal to the calculated joint angle, the desired shape and path will be attained. For each and every segment of the array, all applicable joint angles may be calculated within that segment, and all corresponding actuators will be activated, if necessary, to the extent needed in order to achieve the desired array configuration. With the assistance of a microprocessor unit, all of these calculations, measurements, and comparisons may be effected simultaneously readily and rapidly. Upon completion of the cycle or before another array configuration is requested by a user, sufficient power may be required to maintain the positioning or bending of each actuator within the joints and various segments of the array. The degree of holding power will be obviously dependent upon various operating conditions such as surrounding temperature and thermal efficiency of the shape memory alloy array.

Figure 13:
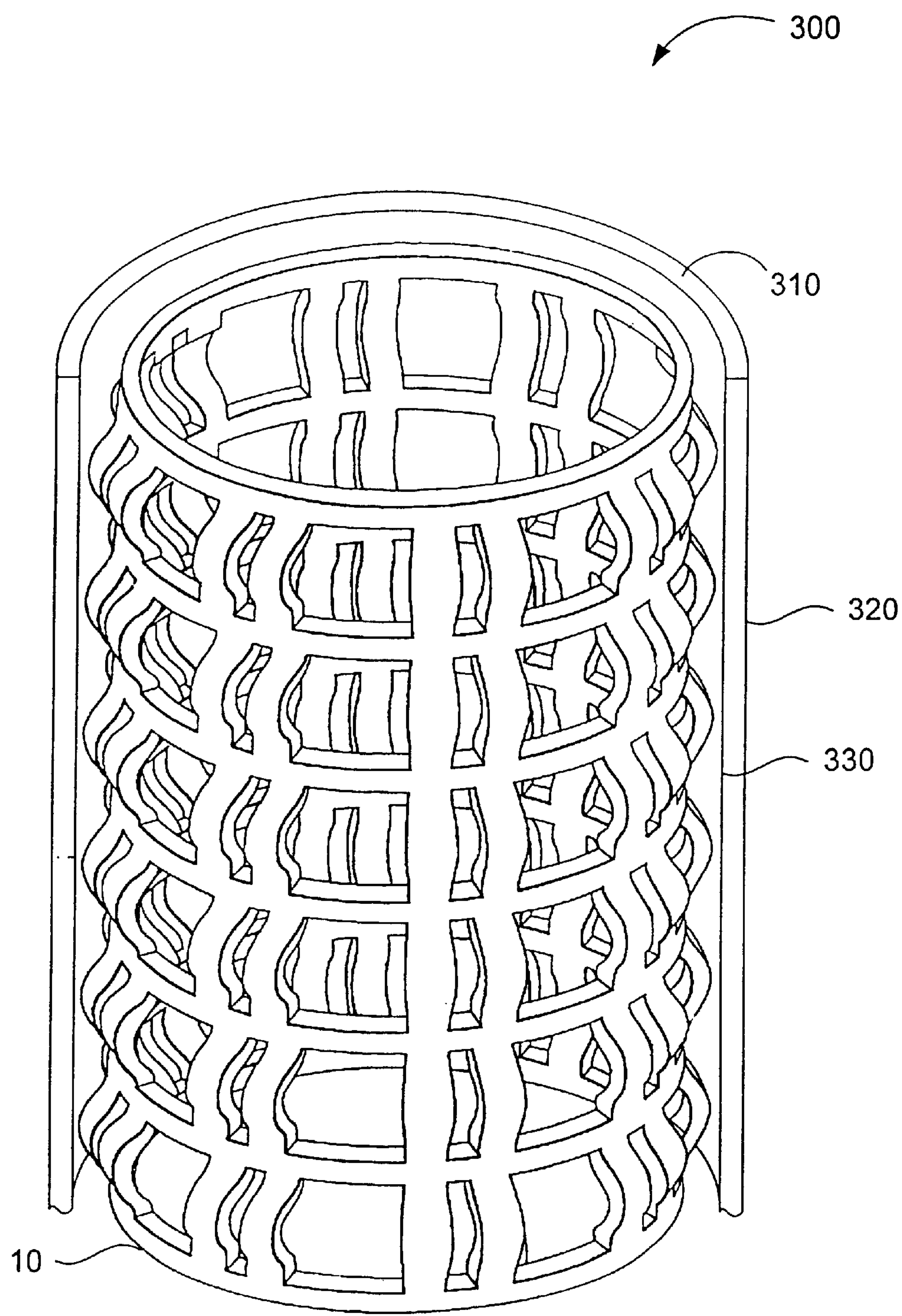
FIG. 13 is a partial perspective view of a catheter including a thin-film shape memory alloy actuator array.

FIG. 13 illustrates a partial perspective view of catheter 300 including thin-film shape memory alloy actuator array 10. Catheter body 310 is shown in cut-away to reveal the presence of actuator array 10 adjacent to the catheter body. Catheter body 310 includes sidewalls 320 and 330. In this example, actuator array 10 is shown adjacent to a portion of the interior sidewall, although actuator array 10 can also be located adjacent to the exterior sidewall 320. Catheter 300 is shown including actuator array 10, although those having skill in the art will readily recognize that any of the disclosed actuators can be implemented as part of a catheter like catheter 300.

While the present invention has been described with reference to the aforementioned applications, this description of the preferred embodiments and methods is not meant to be construed in a limiting sense. It shall be understood that all aspects of the present invention are not limited to the specific depictions, configurations or relative proportions set forth herein which depend upon a variety of conditions and variables. Various modifications in form and detail of the various embodiments of the disclosed invention, as well as other variations of the present invention, will be apparent to a person skilled in the art upon reference to the present disclosure. It is therefore contemplated that the appended claims shall cover any such modifications or variations of the described embodiments as falling within the true spirit and scope of the present invention.

What is claimed is:

1. A shape memory alloy catheter comprising:

a catheter body formed with a sidewall portion;

a shape memory alloy portion positioned adjacent the catheter sidewall portion for providing the catheter body with directional movement while in a patient's body, the shape memory alloy portion having a lattice network of individually configured shape memory alloy micro-actuators;

connecting rings wherein the micro-actuators are positioned in between at least two of the connecting rings for separating the micro-actuators into segmented joints; and an addressable thin-film heater element in communication with the shape memory alloy portion for activation of selected micro-actuators, wherein the shape memory alloy portion includes at least one micro-actuator that expands upon heating by an addressable heater element and at least one micro-actuator that contracts upon heating by another addressable heater element.

2. The shape memory alloy catheter as recited in claim 1, wherein the shape memory alloy portion includes at least one addressable heater element to heat a selected combination of at least one micro-actuator for varying the relative stiffness of the shape memory alloy portion.

3. The shape memory alloy catheter as recited in claim 2 wherein the shape memory alloy portion may be thermally activated to have a different stiffness relative to the catheter sidewall portion.

4. The shape memory alloy catheter as recited in claim 1 wherein the shape memory alloy portion surrounds at least a portion of the catheter body.

5. The shape memory alloy catheter as recited in claim 1 wherein the shape memory alloy is NiTi.

6. The shape memory alloy catheter of claim 1 wherein at least two of the individually configured shape memory alloy micro-actuators are formed from a single piece of shape memory alloy material.

7. The shape memory alloy catheter as recited in claim 1 further including a micro-fabricated sensor.

8. The shape memory alloy catheter of claim 1 further including a micro-fabricated transducer.

9. A shape memory alloy catheter comprising:

a catheter body formed with a sidewall portion;

a shape memory alloy portion positioned adjacent the catheter sidewall portion, for providing the catheter body with directional movement while in a patient's body, the shape memory alloy portion having a lattice network of individually configured shape memory alloy micro-actuators, wherein the micro-actuators are arranged in segmented joints;

an addressable thin-film heater element fixed to a surface of the shape memory alloy portion for activation of selected micro-actuators;

a micro-fabricated sensor; and connecting rings wherein the micro-actuators are positioned in between at least two of the connecting rings for separating the micro-actuators into segmented joints.

10. The shape memory alloy catheter as recited in claim 9 wherein the shape memory alloy portion includes at least one micro-actuator that expands upon heating by an addressable heater element and at least one micro-actuator that contracts upon heating by another addressable heater element.

11. A shape memory alloy catheter comprising:

a catheter body formed with a sidewall portion;

a shape memory alloy portion positioned adjacent the catheter sidewall portion for providing the catheter body with directional movement while in a patient'a body, the shape memory alloy portion having a lattice network of individually configured shape memory alloy micro-actuators; fixed to a surface of an addressable thin-film heater element fixed to a surface of the shape memory alloy portion for activation of selected micro-actuators; and a micro-fabricated sensor, wherein at least two of the individually configured shape memory alloy micro-actuators are formed from a single piece of shape memory alloy material.

12. The shape memory alloy catheter as recited in claim 11 wherein the addressable thin-film heater element is operable to heat at least one micro-actuator for varying the relative stiffness of the shape memory alloy portion.

13. The shape memory alloy catheter as recited in claim 12 wherein the shape memory alloy portion may be thermally activated to have a different stiffness relative to the catheter sidewall portion.

14. The shape memory alloy catheter as recited in claim 11 wherein the shape memory alloy portion surrounds at least a portion of the catheter body.

15. The shape memory alloy catheter as recited in claim 11 wherein the shape memory alloy is NiTi.

16. The shape memory alloy catheter of claim 11 further including a micro-fabricated transducer.

17. A shape memory alloy catheter comprising:

a catheter body formed with a sidewall portion;

a shape memory alloy portion positioned adjacent the catheter sidewall portion for providing the catheter body with directional movement while in a patient's body, the shape memory alloy portion having a lattice network of individually configured shape memory alloy micro-actuators, wherein the micro-actuators are arranged in segmented joints;

an addressable thin-film heater element fixed to a surface of the shape memory alloy portion for activation of selected micro-actuators;

a micro-fabricated transducer; and connecting rings wherein the micro-actuators are positioned in between at least two of the connecting rings for separating the micro-actuators into segmented joints.

18. The shape memory alloy catheter as recited in claim 17 wherein the shape memory alloy portion includes at least one micro-actuator that expands upon heating by an addressable heater element and at least one micro-actuator that contracts upon heating by another addressable heater element.

19. A shape memory alloy catheter comprising:

a catheter body formed with a sidewall portion;

a shape memory alloy portion positioned adjacent the catheter sidewall portion for providing the catheter body with directional movement while in a patient's body, the shape memory alloy portion having a lattice network of individually configured shape memory alloy micro-actuators; connecting rings wherein the micro-actuators are positioned in between at least two of the connecting rings for separating the micro-actuators into segmented joints an addressable thin-film heater element fixed to the surface of the shape memory alloy portion for activation of selected micro-actuators; and a micro-fabricated transducer, wherein at least two of the individually configured shape memory alloy micro-actuators are formed from a single piece of shape memory alloy material.

20. The shape memory alloy catheter as recited in claim 19 wherein the addressable thin-film heater element is operable to heat at least one micro-actuator for varying the relative stiffness of the shape memory alloy portion.

21. The shape memory alloy catheter as recited in claim 20 wherein the shape memory alloy portion may be thermally activated to have a different stiffness relative to the catheter sidewall portion.

22. The shape memory alloy catheter as recited in claim 19 wherein the shape memory alloy portion surrounds at least a portion of the catheter body.

23. The shape memory alloy catheter as recited in claim 19 further including a micro-fabricated sensor.

24. The shape memory alloy catheter as recited in claim 19 wherein the shape memory alloy is NiTi.

* * * * *